United States Patent
Jang et al.

(10) Patent No.: US 12,409,203 B2
(45) Date of Patent: Sep. 9, 2025

(54) POLYPEPTIDE DIMER WITH HIGH SIALIC ACID CONTENT, COMPRISING EXTRACELLULAR DOMAIN OF ALPHA SUBUNIT OF IGE FC RECEPTOR, AND PHARMACEUTICAL COMPOSITION COMPRISING SAME

(71) Applicant: GI INNOVATION, INC., Seoul (KR)

(72) Inventors: Myoung Ho Jang, Seoul (KR); Bo-Gie Yang, Seoul (KR); Kyungwha Lee, Gyeonggi-do (KR)

(73) Assignee: GI INNOVATION, INC., Seoul (KR)

( * ) Notice: Subject to any disclaimer, the term of this patent is extended or adjusted under 35 U.S.C. 154(b) by 762 days.

(21) Appl. No.: 17/625,668

(22) PCT Filed: Jul. 7, 2020

(86) PCT No.: PCT/KR2020/008855
§ 371 (c)(1),
(2) Date: Jan. 7, 2022

(87) PCT Pub. No.: WO2021/006599
PCT Pub. Date: Jan. 14, 2021

(65) Prior Publication Data
US 2022/0257693 A1    Aug. 18, 2022

(30) Foreign Application Priority Data
Jul. 8, 2019    (KR) .................. 10-2019-0082217

(51) Int. Cl.
*A61K 38/00*    (2006.01)
*A23L 33/18*    (2016.01)
(Continued)

(52) U.S. Cl.
CPC .............. *A61K 38/00* (2013.01); *A23L 33/18* (2016.08); *A61K 9/0019* (2013.01);
(Continued)

(58) Field of Classification Search
CPC ....... A61K 38/00; A61K 9/0019; A23L 33/18; A61P 37/08; A61P 11/06; C07K 14/70535; C07K 2319/00; A23V 2200/304
See application file for complete search history.

(56) References Cited

U.S. PATENT DOCUMENTS

2008/0300188 A1    12/2008    Yang et al.
2013/0217864 A1    8/2013    Cho et al.
(Continued)

FOREIGN PATENT DOCUMENTS

CN    105175553 A    12/2015
CN    107207623 A    9/2017
(Continued)

OTHER PUBLICATIONS

English translation of Hu et al. (CN101633698A). (Year: 2010).*
(Continued)

*Primary Examiner* — Robert B Mondesi
*Assistant Examiner* — Naghmeh Nina Moazzami
(74) *Attorney, Agent, or Firm* — Sughrue Mion, PLLC

(57) ABSTRACT

A modified IgE Fc receptor having a high content of sialic acid and a pharmaceutical composition contains the modified IgE Fc receptor are disclosed. The polypeptide dimer having a high content of sialic acid not only has excellent safety and persistence in a body as compared with conventionally used anti-IgE antibodies, but also shows strong binding to IgE. Thus, the polypeptide has the advantage of an extended administration cycle. The polypeptide dimer is also an IgE single target substance, and unlike conventional anti-IgE antibodies to which the Fc of IgG1 is applied, does not bind to an Fc gamma receptor. The polypeptide dimer
(Continued)

can be usefully used for the prevention or treatment of allergic diseases.

13 Claims, 18 Drawing Sheets

Specification includes a Sequence Listing.

(51) Int. Cl.
| | |
|---|---|
| A61K 9/00 | (2006.01) |
| A61K 9/70 | (2006.01) |
| A61P 37/08 | (2006.01) |
| C07K 14/735 | (2006.01) |

(52) U.S. Cl.
CPC ............ *A61K 9/7023* (2013.01); *A61P 37/08* (2018.01); *C07K 14/70535* (2013.01); *C07K 2319/30* (2013.01)

(56) References Cited

U.S. PATENT DOCUMENTS

| | | |
|---|---|---|
| 2016/0024179 A1 | 1/2016 | Warner et al. |
| 2017/0158746 A1 | 6/2017 | Yang et al. |
| 2017/0189476 A1 | 7/2017 | Sung et al. |
| 2018/0319858 A1 | 11/2018 | Kang et al. |
| 2019/0127438 A1 | 5/2019 | Smrzka et al. |
| 2021/0070833 A1 | 3/2021 | Sung et al. |
| 2022/0347236 A1 | 11/2022 | Jang et al. |

FOREIGN PATENT DOCUMENTS

| | | |
|---|---|---|
| EP | 3 260 469 A1 | 12/2017 |
| EP | 3 738 599 A1 | 11/2020 |
| JP | 2000-516089 A | 12/2000 |
| JP | 2010-531134 A | 9/2010 |
| JP | 2019-510737 A | 4/2019 |
| JP | 7041272 B2 | 3/2022 |
| JP | 7128291 B2 | 8/2022 |
| JP | 2022-176971 A | 11/2022 |
| KR | 2000-0045064 A | 7/2000 |
| KR | 10-2012-0116400 A | 10/2012 |
| KR | 10-2012-0135865 A | 12/2012 |
| KR | 10-2017-0041384 A | 4/2017 |
| KR | 10-1783272 B1 | 9/2017 |
| KR | 10-2017-0120579 A | 10/2017 |
| KR | 10-2019-0084885 A | 7/2019 |
| KR | 10-2019-0084886 A | 7/2019 |
| RU | 2432175 C2 | 10/2011 |
| WO | 98/04718 A1 | 2/1998 |
| WO | 2008/012528 A1 | 1/2008 |
| WO | 2008028068 A2 | 3/2008 |
| WO | 2008/147143 A2 | 12/2008 |
| WO | 2010033736 A1 | 3/2010 |
| WO | 2012/053828 A | 4/2012 |
| WO | 2012/169735 A2 | 12/2012 |
| WO | 2016/133197 A1 | 8/2016 |
| WO | 2017061780 A1 | 4/2017 |
| WO | 2019135666 A1 | 7/2019 |
| WO | 2019135668 A1 | 7/2019 |

OTHER PUBLICATIONS

English translation of Woo et al. (KR20170041384A). (Year: 2017).*
Byrne et al., Sialic acids: carbohydrate moieties that influence the biological and physical properties of biopharmaceutical proteins and living cells, Drug Discovery Today, vol. 12 Nos. 7/8 Apr. 2007, pp. 319-326 (Year: 2007).*
Office Action issued May 7, 2024 in Japanese Application No. 2021-575270.
Takahashi, Kyoko et al., "The High Affinity IgE Receptor (FceRI) as a Target for Anti-allergic Agents", Allergology International. 2005; vol. 54, No. 1, pp. 1-6.
David Dombrowicz, et al., "Absence of FcεRIα Chain Results in Upregulation of FcγRIII-dependent Mast Cell Degranulation and Anaphylaxis", Role of FcγRIII in Mouse Active Anaphylaxis, The Journal of Clinical Investigation, vol. 99, No. 5, Mar. 1997, pp. 915-925.
Irving C. Allen, "Mouse Models of Allergic Disease: Methods and Protocols", Springer Protocols, Humana Press, Methods in Molecular Biology, 2013, vol. 1032, DOI 10.1007/978-1-62703-496-8_24.
International Search Report for PCT/KR2020/008855 dated Oct. 19, 2020.
Written Opinion for PCT/KR2020/008855 dated Oct. 19, 2020.
European Patent Office, Communication issued Dec. 19, 2022 in copending Application No. 20 83 7726.
"Immunoglobulin delta-chain, partial [*Homo sapiens*]", GenBank: AAA52771.1, Aug. 1, 2016 (3 pages) Accessed via the Internet: https://www.ncbi.ntm.nih.gov/protein/aaa52771.1 last visited Feb. 8, 2023.
"Immunoglobulin delta-chain, partial [*Homo sapiens*]", GenBank: AAA52770.1, Aug. 1, 2016 (3 pages) Accessed via the Internet: https://www.ncbi.ntm.nih.gov/protein/495871/ last visited Jul. 5, 2023.
Japanese Office Action dated Oct. 9, 2024 in JP Application No. 2021-575270.
Russian Office Action dated Dec. 5, 2024 in RU Application No. 2022102827/10.

* cited by examiner

SEQUENCE LISTING

<160> NUMBER OF SEQ ID NOS: 22

<210> SEQ ID NO 1
<211> LENGTH: 180
<212> TYPE: PRT
<213> ORGANISM: Artificial Sequence
<220> FEATURE:
<223> OTHER INFORMATION: FCeRI1 ECD

<400> SEQUENCE: 1

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln
            180

<210> SEQ ID NO 2
<211> LENGTH: 215
<212> TYPE: PRT
<213> ORGANISM: Artificial Sequence
<220> FEATURE:
<223> OTHER INFORMATION: Modified Fc

<400> SEQUENCE: 2

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
                20                  25                  30

Asp Val Ser Gln Glu Asp Pro Glu Val Gln Phe Asn Trp Tyr Val Asp
            35                  40                  45

Gly Val Glu Val His Asn Ala Lys Thr Lys Pro Arg Glu Glu Gln Phe
        50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

```
Glu Pro Gln Val Tyr Thr Leu Pro Ser Gln Glu Met Thr Lys
            115                 120                 125
Asn Gln Val Ser Leu Thr Cys Leu Val Lys Gly Phe Tyr Pro Ser Asp
130                 135                 140
Ile Ala Val Glu Trp Glu Ser Asn Gly Gln Pro Glu Asn Asn Tyr Lys
145                 150                 155                 160
Thr Thr Pro Pro Val Leu Asp Ser Asp Gly Ser Phe Phe Leu Tyr Ser
                165                 170                 175
Arg Leu Thr Val Asp Lys Ser Arg Trp Gln Gly Asn Val Phe Ser
            180                 185                 190
Cys Ser Val Met His Glu Ala Leu His Asn His Tyr Thr Gln Lys Ser
            195                 200                 205
Leu Ser Leu Ser Leu Gly Lys
    210                 215

<210> SEQ ID NO 3
<211> LENGTH: 30
<212> TYPE: PRT
<213> ORGANISM: Artificial Sequence
<220> FEATURE:
<223> OTHER INFORMATION: IgD hinge variant

<400> SEQUENCE: 3

Arg Asn Thr Gly Arg Gly Gly Glu Glu Lys Lys Gly Ser Lys Glu Lys
1               5                   10                  15
Glu Glu Gln Glu Glu Arg Glu Thr Lys Thr Pro Glu Cys Pro
            20                  25                  30

<210> SEQ ID NO 4
<211> LENGTH: 49
<212> TYPE: PRT
<213> ORGANISM: Artificial Sequence
<220> FEATURE:
<223> OTHER INFORMATION: IgD hinge variant

<400> SEQUENCE: 4

Ala Gln Pro Gln Ala Glu Gly Ser Leu Ala Lys Ala Thr Thr Ala Pro
1               5                   10                  15
Ala Thr Thr Arg Asn Thr Gly Arg Gly Gly Glu Glu Lys Lys Gly Ser
            20                  25                  30
Lys Glu Lys Glu Glu Gln Glu Glu Arg Glu Thr Lys Thr Pro Glu Cys
            35                  40                  45
Pro

<210> SEQ ID NO 5
<211> LENGTH: 540
<212> TYPE: DNA
<213> ORGANISM: Artificial Sequence
<220> FEATURE:
<223> OTHER INFORMATION: nucleotides sequence of FCeRI1 ECD

<400> SEQUENCE: 5
gtgccccaga agcccaaggt gagcctgaac cctccctgga cagaatcttc aagggcgag      60 aacgtgaccc tgacctgcaa cggcaacaac ttcttcgagg tgagcagcac caagtggttc    120
cacaatggca gcctgagcga ggagaccaac agctccctga catcgtgaa cgccaagttc     180 gaggacagcg gcgagtacaa gtgccagcac cagcaggtga cgagagcga gcccgtgtac    240 ctggaggtgt tcagcgactg gctgctgctg caggccagcg ccgaggtggt gatgagggc    300 cagccctgt tcctgagatg ccacggctgg agaaactggg acgtgtacaa ggtgatctac   360
```

```
tacaaggatg cgcaggccct gaagtactgg tacgagaacc acaacatctc catcaccaac    420
gccaccgtgg aggacagcgg cacctactac tgcacaggca aggtgtggca gctggactac    480
gagagcgagc ccctgaacat caccgtgatc aaggctccca gagagaagta ctggctgcag    540
```

<210> SEQ ID NO 6
<211> LENGTH: 561
<212> TYPE: DNA
<213> ORGANISM: Artificial Sequence
<220> FEATURE:
<223> OTHER INFORMATION: nucleotides sequence of modified Fc

<400> SEQUENCE: 6

```
tgcgtggtcg tggatgtgag ccaggaagat cccgaagtgc agttcaactg gtacgtggat     60
ggcgtggaag tgcacaacgc caagaccaag cccagagaag agcagttcaa ctccacctac    120
agagtggtga gcgtgctgac cgtgctgcac caggactggc tgaacggcaa ggagtacaag    180
tgcaaggtgt ccaacaaagg cctgcccagc tccatcgaga agaccatcag caaagccaaa    240
ggccagccca gagaacccca ggtgtacacc ctgcctccca gcaggaagaa gatgaccaag    300
aaccaggtgt ccctgacctg cctggtgaaa ggcttctacc ccagcgacat cgccgtggag    360
tgggaaagca acggccagcc cgagaacaat tacaagacaa cccctcccgt gctggatagc    420
gatggcagct ctttctgta cagcagactg accgtggaca gagcagatg gcaggaaggc      480 aacgtgttca gctgcagcgt gatgcacgaa gccctgcaca accactacac ccagaagagc    540
ctgtccctga gcctgggcaa g                                              561
```

<210> SEQ ID NO 7
<211> LENGTH: 174
<212> TYPE: DNA
<213> ORGANISM: Artificial Sequence
<220> FEATURE:
<223> OTHER INFORMATION: nucleotides sequence of IgD hinge variant

<400> SEQUENCE: 7

```
aggaacaccg gcagaggagg cgaggaaaag aaaggaagca aggagaagga ggagcaggag     60
gaaagagaaa ccaagacccc cgagtgcccc agccacaccc agcccctggg cgtgttcctg    120
ttccccccca agcccaagga caccctgatg atcagcagaa cccccgaggt gacc           174
```

<210> SEQ ID NO 8
<211> LENGTH: 231
<212> TYPE: DNA
<213> ORGANISM: Artificial Sequence
<220> FEATURE:
<223> OTHER INFORMATION: nucleotides sequence of IgD hinge variant

<400> SEQUENCE: 8

```
gcccagcccc aggccgaggg cagcctggct aaggccacca cagctcccgc caccaccagg     60
aacaccggca gaggaggcga ggaaaagaaa ggaagcaagg agaaggagga gcaggaggaa    120
agagaaacca agaccccga gtgccccagc cacacccagc ccctgggcgt gttcctgttc     180 cccccaagc caaggacac cctgatgatc agcagaaccc ccgaggtgac c                231
```

<210> SEQ ID NO 9
<211> LENGTH: 25
<212> TYPE: PRT
<213> ORGANISM: Artificial Sequence
<220> FEATURE:
<223> OTHER INFORMATION: signal peptide

```
<400> SEQUENCE: 9

Met Asp Ala Met Leu Arg Gly Leu Cys Cys Val Leu Leu Cys Gly
1               5                   10                  15

Ala Val Phe Val Ser Pro Ser His Ala
            20                  25

<210> SEQ ID NO 10
<211> LENGTH: 75
<212> TYPE: DNA
<213> ORGANISM: Artificial Sequence
<220> FEATURE:
<223> OTHER INFORMATION: nucleotides sequence of signal peptide

<400> SEQUENCE: 10
atggacgcca tgctgagagg cctgtgctgt gtgctgctgc tgtgcggcgc cgtgttcgtg    60
tcccctagcc acgcc                                                    75

<210> SEQ ID NO 11
<211> LENGTH: 450
<212> TYPE: PRT
<213> ORGANISM: Artificial Sequence
<220> FEATURE:
<223> OTHER INFORMATION: FceRIa ECD-hinge-Fc2

<400> SEQUENCE: 11

Met Asp Ala Met Leu Arg Gly Leu Cys Cys Val Leu Leu Cys Gly
1               5                   10                  15

Ala Val Phe Val Ser Pro Ser His Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Arg Asn Thr
        195                 200                 205

Gly Arg Gly Gly Glu Glu Lys Lys Gly Ser Lys Glu Lys Glu Glu Gln
    210                 215                 220

Glu Glu Arg Glu Thr Lys Thr Pro Glu Cys Pro Ser His Thr Gln Pro
225                 230                 235                 240

Leu Gly Val Phe Leu Phe Pro Pro Lys Pro Lys Asp Thr Leu Met Ile
                245                 250                 255
```

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 12
<211> LENGTH: 1350
<212> TYPE: DNA
<213> ORGANISM: Artificial Sequence
<220> FEATURE:
<223> OTHER INFORMATION: nucleotides sequence of FceRIa ECD-hinge-Fc2

<400> SEQUENCE: 12
atggacgcca tgctgagagg cctgtgctgt gtgctgctgc tgtgcggcgc cgtgttcgtg      60
tcccctagcc acgccgtgcc ccagaagccc aaggtgagcc tgaaccctcc ctggaacaga     120
atcttcaagg gcgagaacgt gaccctgacc tgcaacggca caacttctt cgaggtgagc     180 agcaccaagt ggttccacaa tggcagcctg agcgaggaga ccaacagctc cctgaacatc     240
gtgaacgcca agttcgagga cagcggcgag tacaagtgcc agcaccagca ggtgaacgag     300
agcgagcccg tgtacctgga ggtgttcagc gactggctgc tgctgcaggc cagcgccgag     360
gtggtgatgg agggccagcc cctgttcctg agatgccacg gctggagaaa ctgggacgtg     420
tacaaggtga tctactacaa ggatggcgag gccctgaagt actggtacga gaaccacaac     480
atctccatca ccaacgccac cgtggaggac agcggcacct actactgcac aggcaaggtg     540
tggcagctgg actacgagag cgagcccctg aacatcaccg tgatcaaggc tcccagagag     600
aagtactggc tgcagaggaa caccggcaga ggaggcgagg aaaagaaagg aagcaaggag     660
aaggaggagc aggaggaaag agaaaccaag accccgagt gccccagcca cccagccc     720 ctgggcgtgt cctgttccc ccccaagccc aaggacaccc tgatgatcag cagaaccccc     780
gaggtgacct gcgtggtcgt ggatgtgagc caggaagatc ccgaagtgca gttcaactgg     840
tacgtggatg gcgtggaagt gcacaacgcc aagaccaagc ccagagaaga gcagttcaac     900

```
tccacctaca gagtggtgag cgtgctgacc gtgctgcacc aggactggct gaacggcaag    960
gagtacaagt gcaaggtgtc caacaaaggc ctgcccagct ccatcgagaa gaccatcagc   1020
aaagccaaag gccagcccag agaacccag gtgtacaccc tgcctccag ccaggaagag     1080 atgaccaaga accaggtgtc cctgacctgc ctggtgaaag gcttctaccc cagcgacatc   1140
gccgtggagt gggaaagcaa cggccagccc gagaacaatt acaagacaac ccctcccgtg   1200
ctggatagcg atggcagctt ctttctgtac agcagactga ccgtggacaa gagcagatgg   1260
caggaaggca acgtgttcag ctgcagcgtg atgcacgaag ccctgcacaa ccactacacc   1320
cagaagagcc tgtccctgag cctgggcaag                                    1350
```

<210> SEQ ID NO 13
<211> LENGTH: 469
<212> TYPE: PRT
<213> ORGANISM: Artificial Sequence
<220> FEATURE:
<223> OTHER INFORMATION: FceRIa ECD-hinge-Fc3

<400> SEQUENCE: 13

```
Met Asp Ala Met Leu Arg Gly Leu Cys Cys Val Leu Leu Cys Gly
1               5                   10                  15

Ala Val Phe Val Ser Pro Ser His Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Ala Gln Pro
        195                 200                 205

Gln Ala Glu Gly Ser Leu Ala Lys Ala Thr Thr Ala Pro Ala Thr Thr
    210                 215                 220

Arg Asn Thr Gly Arg Gly Gly Glu Glu Lys Lys Gly Ser Lys Glu Lys
225                 230                 235                 240

Glu Glu Gln Glu Glu Arg Glu Thr Lys Thr Pro Glu Cys Pro Ser His
                245                 250                 255

Thr Gln Pro Leu Gly Val Phe Leu Phe Pro Pro Lys Pro Lys Asp Thr
            260                 265                 270

Leu Met Ile Ser Arg Thr Pro Glu Val Thr Cys Val Val Val Asp Val
```

```
                  275                 280                 285
Ser Gln Glu Asp Pro Glu Val Gln Phe Asn Trp Tyr Val Asp Gly Val
                290                 295                 300

Glu Val His Asn Ala Lys Thr Lys Pro Arg Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
                340                 345                 350

Ser Ile Glu Lys Thr Ile Ser Lys Ala Lys Gly Gln Pro Arg Glu Pro
                355                 360                 365

Gln Val Tyr Thr Leu Pro Pro Ser Gln Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
                420                 425                 430

Thr Val Asp Lys Ser Arg Trp Gln Glu Gly Asn Val Phe Ser Cys Ser
                435                 440                 445

Val Met His Glu Ala Leu His Asn His Tyr Thr Gln Lys Ser Leu Ser
                450                 455                 460

Leu Ser Leu Gly Lys
465

<210> SEQ ID NO 14
<211> LENGTH: 1407
<212> TYPE: DNA
<213> ORGANISM: Artificial Sequence
<220> FEATURE:
<223> OTHER INFORMATION: nucleotides sequence of FceRIa ECD-hinge-Fc3

<400> SEQUENCE: 14
atggacgcca tgctgagagg cctgtgctgt gtgctgctgc tgtgcggcgc cgtgttcgtg      60
tcccctagcc acgccgtgcc ccagaagccc aaggtgagcc tgaaccctcc ctggaacaga     120
atcttcaagg gcgagaacgt gaccctgacc tgcaacggca caacttcttc cgaggtgagc     180
agcaccaagt ggttccacaa tggcagcctg agcgaggaga ccaacagctc cctgaacatc     240
gtgaacgcca gttcgagga cagcggcgag tacaagtgcc agcaccagca ggtgaacgag     300
agcgagcccg tgtacctgga ggtgttcagc gactggctgc tgctgcaggc cagcgccgag     360
gtggtgatgg agggccagcc cctgttcctg agatgccacg ctggagaaaa ctgggacgtg     420
tacaaggtga tctactacaa ggatggcgag gccctgaagt actggtacga gaaccacaac     480
atctccatca ccaacgccac cgtggaggac agcggcacct actactgcac aggcaaggtg     540
tggcagctgg actacgagag cgagcccctg aacatcaccg tgatcaaggc tcccagagag     600
aagtactggc tgcaggccca gccccaggcc gagggcagcc tggctaaggc caccacagct     660
cccgccacca ccaggaacac cggcagagga ggcgaggaaa agaaaggaag caaggagaag     720
gaggagcagg aggaaagaga accaagacc cccgagtgcc cagccacac ccagccctg     780 ggcgtgttcc tgttcccccc caagcccaag gacaccctga tgatcagcag aacccccgag     840
gtgacctgcg tggtcgtgga tgtgagccag gaagatcccg aagtgcagtt caactggtac     900
gtggatggcg tggaagtgca caacgccaag accaagccca gagaagagca gttcaactcc     960
```

```
acctacagag tggtgagcgt gctgaccgtg ctgcaccagg actggctgaa cggcaaggag    1020
tacaagtgca aggtgtccaa caaaggcctg cccagctcca tcgagaagac catcagcaaa    1080
gccaaaggcc agcccagaga accccaggtg tacaccctgc ctcccagcca ggaagagatg    1140
accaagaacc aggtgtccct gacctgcctg gtgaaaggct tctacccag cgacatcgcc     1200 gtggagtggg aaagcaacgg ccagcccgag aacaattaca agacaaccc tcccgtgctg    1260 gatagcgatg gcagcttctt tctgtacagc agactgaccg tggacaagag cagatggcag    1320
gaaggcaacg tgttcagctg cagcgtgatg cacgaagccc tgcacaacca ctacacccag    1380
aagagcctgt ccctgagcct gggcaag                                       1407
```

<210> SEQ ID NO 15
<211> LENGTH: 406
<212> TYPE: PRT
<213> ORGANISM: Artificial Sequence
<220> FEATURE:
<223> OTHER INFORMATION: human a-2,6 sialic acid transferase

<400> SEQUENCE: 15

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
                20                  25                  30

Ser Tyr Tyr Asp Ser Phe Lys Leu Gln Thr Lys Glu Phe Gln Val Leu
                35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
                115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
                180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
```

|     |     | 275 |     |     | 280 |     |     |     | 285 |     |     |
| --- | --- | --- | --- | --- | --- | --- | --- | --- | --- | --- | --- |

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
                355                 360                 365

Tyr His Pro Leu Leu Tyr Glu Lys Asn Leu Val Lys His Leu Asn Gln
            370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 16
<211> LENGTH: 1218
<212> TYPE: DNA
<213> ORGANISM: Artificial Sequence
<220> FEATURE:
<223> OTHER INFORMATION: nucleotides sequence of human a-2,6 sialic acid
      transferase

<400> SEQUENCE: 16

```
atgatccaca ccaacctgaa gaagaagttc agctgctgcg tgctggtgtt cctgctgttc      60
gccgtgatct gcgtgtggaa ggagaagaag aaaggcagct actacgacag cttcaagctg     120
cagaccaagg agttccaggt gctgaagagc ctgggcaagc tggccatggg cagcgacagc     180
cagagcgtgt ccagctcctc cacccaggat ccccacagag cagacagac cctgggcagc     240 ctgagaggcc tggccaaggc caagcccgag gccagcttcc aggtgtggaa caaggacagc     300
agcagcaaga acctgatccc cagactgcag aagatctgga gaactaccct gagcatgaac     360
aagtacaagg tgagctacaa aggacccgga cccggcatca gttcagcgc cgaggccctg     420 aggtgccacc tgagagacca cgtgaacgtg agcatggtgg aagtgaccga cttcccttc     480 aacaccagcg agtgggaagg ctacctgccc aaggagagca tcaggaccaa ggctggcccc     540
tggggcagat gcgccgtggt gagcagcgct ggcagcctga gagctccca gctgggcaga     600 gagatcgacg accacgatgc cgtgctgagg ttcaatggcg ctcccaccgc caacttccag     660
caggacgtgg gcaccaagac cacaatccgg ctgatgaaca gccagctggt gacaaccgag     720
aagcggttcc tgaaggacag cctgtacaac gagggcatcc tgatcgtgtg ggatcccagc     780
gtgtaccaca gcgacatccc caagtggtac cagaatcccg actacaactt cttcaacaac     840
tacaagacct atagaaagct gcaccccaac cagcccttct acatcctgaa gccccagatg     900
ccctgggagc tgtgggacat cctgcaggag atcagccctg aagagatcca gcccaaccct     960
ccctccagcg gcatgctggg cattatcatc atgatgaccc tgtgcgacca ggtggacatc    1020
tacgagttcc tgcccagcaa gagaaagacc gacgtgtgct actactatca agttcttc      1080 gacagcgcct gcaccatggg cgcctaccac cccctgctgt acgagaagaa cctggtgaag    1140
cacctgaacc agggcaccga cgaggacatc tacctgctgg gcaaagccac cctgcccggc    1200
ttcagaacca tccactgc                                                   1218
```

```
<210> SEQ ID NO 17
<211> LENGTH: 30
<212> TYPE: PRT
<213> ORGANISM: Artificial Sequence
<220> FEATURE:
<221> NAME/KEY: MISC_FEATURE
<222> LOCATION: (12)
<223> OTHER INFORMATION: Xaa is Lys or Gly
<220> FEATURE:
<221> NAME/KEY: MISC_FEATURE
<222> LOCATION: (13)
<223> OTHER INFORMATION: Xaa is Glu, Gly, or Ser
<220> FEATURE:
<223> OTHER INFORMATION: IgD hinge variant

<400> SEQUENCE: 17

Arg Asn Thr Gly Arg Gly Gly Glu Glu Lys Lys Xaa Xaa Lys Glu Lys
1               5                   10                  15

Glu Glu Gln Glu Glu Arg Glu Thr Lys Thr Pro Glu Cys Pro
            20                  25                  30

<210> SEQ ID NO 18
<211> LENGTH: 49
<212> TYPE: PRT
<213> ORGANISM: Artificial Sequence
<220> FEATURE:
<221> NAME/KEY: MISC_FEATURE
<222> LOCATION: (31)
<223> OTHER INFORMATION: Xaa is Lys or Gly
<220> FEATURE:
<221> NAME/KEY: MISC_FEATURE
<222> LOCATION: (32)
<223> OTHER INFORMATION: Xaa is Glu, Gly, or Ser
<220> FEATURE:
<223> OTHER INFORMATION: IgD hinge variant

<400> SEQUENCE: 18

Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Glu Lys Lys Xaa Xaa
            20                  25                  30

Lys Glu Lys Glu Glu Gln Glu Glu Arg Glu Thr Lys Thr Pro Glu Cys
        35                  40                  45

Pro

<210> SEQ ID NO 19
<211> LENGTH: 30
<212> TYPE: PRT
<213> ORGANISM: Artificial Sequence
<220> FEATURE:
<223> OTHER INFORMATION: IgD hinge

<400> SEQUENCE: 19

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro
            20                  25                  30

<210> SEQ ID NO 20
<211> LENGTH: 425
<212> TYPE: PRT
<213> ORGANISM: Artificial Sequence
<220> FEATURE:
<223> OTHER INFORMATION: FceRIa ECD-hinge-Fc1

<400> SEQUENCE: 20
```

-continued

```
Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Glu Lys Lys Lys
                180                 185                 190

Glu Lys Glu Lys Glu Glu Gln Glu Arg Glu Thr Lys Thr Pro Glu
            195                 200                 205

Cys Pro Ser His Thr Gln Pro Leu Gly Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
```

<210> SEQ ID NO 21
<211> LENGTH: 425
<212> TYPE: PRT
<213> ORGANISM: Artificial Sequence
<220> FEATURE:
<223> OTHER INFORMATION: FceRIa ECD-hinge-Fc2

<400> SEQUENCE: 21

```
Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Glu Glu Lys Lys Gly
            180                 185                 190

Ser Lys Glu Lys Glu Glu Gln Glu Glu Arg Glu Thr Lys Thr Pro Glu
        195                 200                 205

Cys Pro Ser His Thr Gln Pro Leu Gly Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
```

```
              355                 360                 365
Tyr Lys Thr Thr Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
    420                 425

<210> SEQ ID NO 22
<211> LENGTH: 444
<212> TYPE: PRT
<213> ORGANISM: Artificial Sequence
<220> FEATURE:
<223> OTHER INFORMATION: FceRIa ECD-hinge-Fc3

<400> SEQUENCE: 22

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Val Asn Glu Ser Glu Pro Val Tyr
65              70                  75                      80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Ala Gln Pro Gln Ala Glu Gly Ser Leu Ala Lys Ala
            180                 185                 190

Thr Thr Ala Pro Ala Thr Thr Arg Asn Thr Gly Arg Gly Gly Glu Glu
        195                 200                 205

Lys Lys Gly Ser Lys Glu Lys Glu Glu Gln Glu Glu Arg Glu Thr Lys
210                 215                 220

Thr Pro Glu Cys Pro Ser His Thr Gln Pro Leu Gly Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
```

```
                  290                 295                 300
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440
```

POLYPEPTIDE DIMER WITH HIGH SIALIC ACID CONTENT, COMPRISING EXTRACELLULAR DOMAIN OF ALPHA SUBUNIT OF IGE FC RECEPTOR, AND PHARMACEUTICAL COMPOSITION COMPRISING SAME

CROSS REFERENCE TO RELATED APPLICATIONS

This application is a National Stage of International Application No. PCT/KR2020/008855 filed Jul. 7, 2020, claiming priority based on Korean Patent Application No. 10-2019-0082217 filed Jul. 8, 2019.

SEQUENCE LISTING

The content of the electronically submitted sequence listing, file name: Sequence_Listing_As_Filed.txt; file size: 36,504 bytes, date of creation: Jan. 1, 2022, filed herewith, is incorporated herein by reference in its entirety.

TECHNICAL FIELD

The present invention relates to a polypeptide dimer comprising an IgE Fc receptor and having a high content of sialic acid and a pharmaceutical composition comprising the same.

BACKGROUND ART

As the modern society is industrialized and eating habits are westernized, the incidence rate of allergic diseases, such as allergic rhinitis, atopic dermatitis, and food allergy, including asthma is increasing. Development of anaphylaxis, a severe allergic disease, is also increasing. These chronic immune diseases severely impair individuals' quality of life and socioeconomic costs are soaring accordingly. Thus, there is a desperate need for measures to overcome such diseases.

Most allergic diseases are caused by an excessive immune response of immunoglobulin E (IgE). IgE is an antibody that is present in blood at a very low concentration under a normal condition. IgE is also usually produced by innocuous antigens. There is a case where the number of IgE is increased without any particular stimulus. Such a case may lead to allergic diseases. The abnormally increased number of IgE can bind to high-affinity IgE Fc receptors (FcεRIs) which are expressed on the surface of mast cells, basophils, and the like. Such binding causes mast cells or basophils to release chemical mediators such as histamine, leukotriene, prostaglandin, bradykinin, and platelet-activating factors. Release of these chemical mediators results in allergic symptoms. In particular, allergic diseases may exhibit worsened symptoms due to the binding between IgE and FcεRI. In addition, FcεRI-expressing cells are known to increase in allergic patients.

Currently, various methods, such as allergen avoidance, administration of anti-allergic drugs, modulation of IgE synthesis in the body, and development of anti-IgE antibodies, have been proposed to treat allergic diseases. However, there still remain many drawbacks, such as insufficient drug efficacy and occurrence of serious side effects. Recently, a composition capable of binding to IgE and FcγRIIb with high affinity and inhibiting cells that express membrane-anchored IgE has been studied. This composition has been reported to be useful for treating IgE-mediated diseases including allergy and asthma (KR10-1783272B).

In particular, omalizumab (trade name: Xolair), which targets an Fc portion of an IgE antibody, has been developed and used as a therapeutic agent for intractable severe asthma and intractable urticaria. However, a high-dose administration of omalizumab to maintain therapeutic effects leads to a high cost burden, and side effects such as angioedema and anaphylactic reaction (The Journal of Clinical Investigation Volume 99, Number 5, March 1997, 915-925).

Besides, from the post-marketing results, serious adverse reactions such as allergic granulomatous vasculitis and idiopathic severe thrombocytopenia have been reported.

DETAILED DESCRIPTION OF THE INVENTION

Technical Problem

Accordingly, the present inventors studied to develop a safe and effective therapeutic agent for allergic diseases. As a result, it was found that when the sialic acid content of a polypeptide dimer comprising two monomers (FcεRIα-ECD) comprising an extracellular domain of an alpha subunit of an IgE Fc receptor is high, the above polypeptide dimer has excellent binding affinity to IgE, as well as maintains a high concentration in the blood. In particular, the present invention was completed by confirming that even when the polypeptide dimer having a high content of sialic acid is administered subcutaneously, effective delivery into the body is possible.

Solution to Problem

An aspect of the present invention provides a polypeptide dimer comprising two monomers comprising an extracellular domain (FcεRIα-ECD) of an alpha subunit of an IgE Fc receptor, wherein the molar ratio of sialic acid/polypeptide dimer is at least 8.

Another aspect of the present invention provides a pharmaceutical composition for preventing or treating allergic diseases, comprising the polypeptide dimer having a high content of sialic acid.

Another aspect of the present invention provides a transdermal patch comprising the pharmaceutical composition.

Another aspect of the present invention provides a topical patch comprising the pharmaceutical composition.

Another aspect of the present invention provides a food composition for ameliorating or alleviating allergic symptoms, comprising the polypeptide dimer having a high content of sialic acid.

Another aspect of the present invention provides a use of the polypeptide dimer having a high content of sialic acid for preventing or treating allergic diseases.

Effect of the Invention

The polypeptide dimer having a high content of sialic acid according to the present invention not only has excellent safety and persistence in the body as compared with conventionally used anti-IgE antibodies, but also binds to IgE very strongly, which has the advantage of an extended administration cycle. In addition, the polypeptide dimer having a high content of sialic acid according to the present invention is an IgE single target substance, and unlike conventional anti-IgE antibodies to which the Fc of IgG1 is applied, does not bind to an Fc gamma receptor. Thus, it can inhibit release of mediators caused by being bound to the Fc gamma receptor on the surface of mast cells, so that severe side effects such as occurrence of anaphylaxis which can be caused by binding between IgG1 and Fc gamma receptor III on mast cells can be minimized. In addition, the polypeptide dimer having a high content of sialic acid can maintain a high concentration in the blood even in the case of subcutaneous administration. Accordingly, the polypeptide dimer having a high content of sialic acid according to the present invention can be usefully used for the prevention or treatment of allergic diseases.

DETAILED DESCRIPTION OF INVENTION

Figure 1:
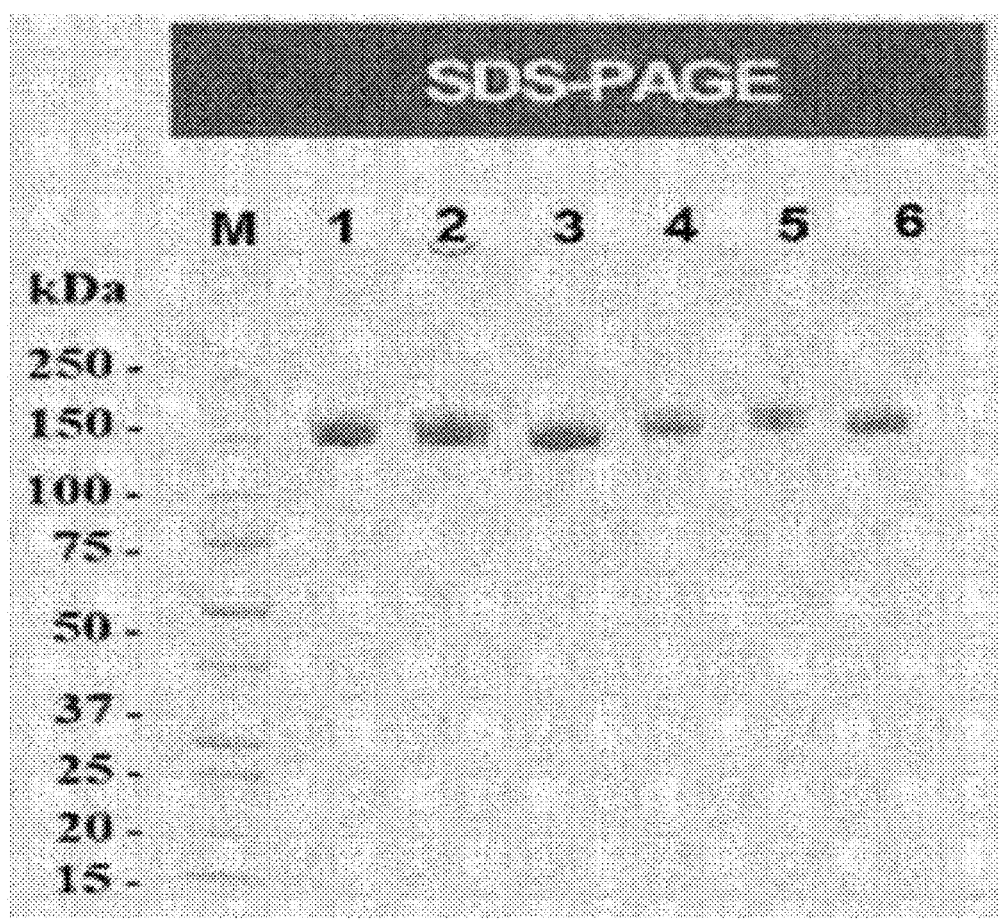
FIG. 1 is a view showing the results of confirming a polypeptide dimer produced in each cell line by SDS-PAGE.

An aspect of the present invention provides a polypeptide dimer having a high content of sialic acid, which comprises two monomers comprising an extracellular domain (FcεRIα-ECD) of an alpha subunit of an IgE Fc receptor, wherein the monomer comprises an Fc region, and the Fc region and FcεRIα-ECD are linked via a hinge, and the polypeptide dimer is characterized in that the molar ratio of sialic acid/polypeptide dimer is at least 8.

As used herein, the term "IgE" means an antibody known as immunoglobulin E. IgE has an affinity to mast cells, basophils, or the like. In addition, reaction between an IgE and an antigen (allergen) corresponding thereto causes an inflammatory reaction. In addition, IgE is known to be a major cause of anaphylaxis.

As used herein, the term "IgE Fc receptor" is also referred to as Fcε receptor and indicates a receptor binding to an Fc portion of IgE. There are two types for the receptor. The receptor having high affinity to IgE Fc is called Fcε receptor I (FcεRI). The receptor having low affinity to IgE Fc is called Fcε receptor II (FcεRII). FcεRI is expressed in mast cells and basophils. In a case where IgE antibodies bound to FcεRI are cross-linked by polyvalent antigens, degranulation occurs in mast cells or basophils, thereby releasing various chemical transmitter substances including histamine. This release leads to an immediate allergic reaction.

The FcεRI is a membrane protein composed of one α chain, one β chain, and two γ chains linked by a disulfide bond. Among these chains, a portion to which IgE binds is the α chain (FcεRIα). FcεRIα has a size of about 60 kDa, and is composed of a hydrophobic domain existing inside the cell membrane and a hydrophilic domain existing outside the cell membrane. In particular, IgE binds to an extracellular domain of the α chain. The FcεRIα can be interchangeably used as the alpha subunit of the IgE Fc receptor.

Specifically, the alpha subunit of the IgE Fc receptor may have the amino acid sequence set forth in NP_001992.1. In addition, the extracellular domain (FcεRIα-ECD) of the alpha subunit of the IgE Fc receptor may have the amino acid sequence of SEQ ID NO: 1. The FcεRIα-ECD may be a fragment or variant of the FcεRIα-ECD, as long as the fragment or variant is capable of binding to IgE. In addition, the FcεRIα-ECD of SEQ ID NO: 1 may be encoded by a polynucleotide having the sequence of SEQ ID NO: 5.

The variant may be prepared through a method of substituting, deleting, or adding one or more amino acids in the wild-type FcεRIα-ECD, as long as the method does not alter a function of the FcεRIα-ECD. Such variant may be 90%, 91%, 92%, 93%, 94%, 95%, 96%, 97%, 98%, 99% or more identical to the amino acid sequence of SEQ ID NO: 1.

Here, the Fc region may be the wild-type Fc region or a modified Fc region. In addition, as used herein, the term "modified Fc region" means a region in which a part of an Fc portion of an antibody has been modified. Here, the Fc region refers to a protein which contains heavy chain constant region 2 (CH2) and heavy chain constant region 3 (CH3) of an immunoglobulin, and does not contain variable regions of heavy and light chains and light chain constant region 1 (CH1) of an immunoglobulin. In particular, the modified Fc region may be obtained by substituting some amino acids in the Fc region or by combining different types of Fc regions. Specifically, the modified Fc region may have the amino acid sequence of SEQ ID NO: 2. In addition, the modified Fc region of SEQ ID NO: 2 may be encoded by a polynucleotide having the sequence of SEQ ID NO: 6.

In addition, the modified Fc region may be sugar chains in a native form, or increased sugar chains relative to a native form. Immunoglobulin Fc sugar chains may be modified by conventional methods such as chemical methods, enzymatic methods, and genetic engineering methods using microorganisms. In addition, the modified Fc region may be a region that lacks antibody dependent cellular cytotoxicity (ADCC) and complement dependent cytotoxicity (CDC) functions due to having no binding site for Fc gamma receptors (FcγR) or complement component 1q (C1q).

In an embodiment, the modified Fc region and the FcεRIα-ECD may be linked via a hinge of an IgD. The hinge may be a hinge region derived from immunoglobulin IgD or a variant thereof. The hinge region of the native IgD is composed of 64 amino acids. The hinge region derived from the immunoglobulin IgD or a variant thereof may be composed of 20 to 60 consecutive amino acids, 25 to 50 consecutive amino acids, or 30 to 40 amino acids. Here, the hinge variant may be obtained by modifying some in the amino acid sequence of the hinge region of IgD in order to minimize generation of truncated forms during a protein production process.

In an embodiment, the hinge region derived from the immunoglobulin IgD or a variant thereof may be composed of 30 or 49 amino acids. In addition, the hinge region derived from the immunoglobulin IgD or a variant thereof may contain at least one cysteine.

In an embodiment, the hinge region derived from the immunoglobulin IgD or a variant thereof may contain the following sequence:

Arg Asn Thr Gly Arg Gly Gly Glu Glu Lys Lys Xaa1 Xaa2 Lys Glu Lys Glu Glu Gln Glu Glu Arg Glu Thr Lys Thr Pro Glu Cys Pro (SEQ ID NO: 17), where Xaa1 may be Lys or Gly, and Xaa2 may be Glu, Gly, or Ser. Specifically, the hinge region derived from the immunoglobulin IgD or a variant thereof may have the amino acid sequence of SEQ ID NO: 3 or SEQ ID NO: 19, thereby minimizing generation of truncated forms during a protein production process.

In another embodiment, the hinge region derived from the immunoglobulin IgD or a variant thereof may contain the following sequence:

Ala Gln Pro Gln Ala Glu Gly Ser Leu Ala Lys Ala Thr Thr Ala Pro Ala Thr Thr Arg Asn Thr Gly Arg Gly Gly Glu Glu Lys Lys Xaa3 Xaa4 Lys Glu Lys Glu Glu Gln Glu Glu Arg Glu Thr Lys Thr Pro Glu Cys Pro (SEQ ID NO: 18), where Xaa3 may be Lys or Gly, and Xaa4 may be Glu, Gly, or Ser. Specifically, the hinge region derived from the immunoglobulin IgD or a variant thereof may have the amino acid sequence of SEQ ID NO: 4, thereby minimizing generation of truncated forms during a protein production process.

In particular, in the hinge region derived from the immunoglobulin IgD or a variant thereof having the sequence of SEQ ID NO: 4, at least one of Thr's may be glycosylated. Specifically, among the amino acids of SEQ ID NO: 18, the 13$^{th}$, 14$^{th}$, 18$^{th}$, or 19$^{th}$ Thr's may be glycosylated. Preferably, all of the four Thr's may be glycosylated. Here, the glycosylation may be O-glycosylation.

The sugar chain attached to the glycoprotein pharmaceuticals is one of the main factors that determine the quality to play an important role in therapeutic efficacy, persistence in the body, targeting and immune response and the like. It was confirmed that a polypeptide dimer in which the end of sugar chain is not terminated with sialic acid was rapidly removed from the body.

The term "sialic acid" used in the present invention may include N-acetylneuraminic acid (Neu5Ac) of Formula 1 below and N-glycolylneuraminic acid (Neu5Gc) of Formula 2 below.

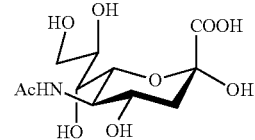

[Formula 1]

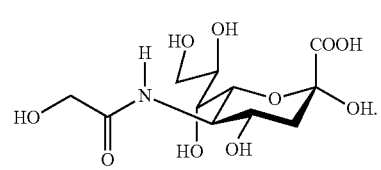

[Formula 2]

In this case, in one embodiment, a polypeptide dimer having a high content of sialic acid may have a high content of N-acetylneuraminic acid.

In addition, a content of sialic acid of a polypeptide dimer may be increased through a purification method. In addition, the content of sialic acid of the polypeptide dimer may be increased by producing a polypeptide dimer in a cell into which a sialic acid transferase gene is introduced.

The polypeptide dimer having a high content of sialic acid may be characterized in that the molar ratio of sialic acid/polypeptide dimer is 8 or more. For example, the molar ratio of sialic acid/polypeptide dimer in the polypeptide dimer having a high content of sialic acid may be 8, 9, 10, 11, 12, 13, 14, 15, 16, 17, 18, 19, 20, 21, 22, 23, 24, 25, 26, 27, 28, 29 or 30. Preferably, the molar ratio of sialic acid/polypeptide dimer in the polypeptide dimer having a high content of sialic acid may be 10, 11, 12, 13, 14, 15, 16, 17, 18, 19, 20, 21, 22, 23, 24 or 25.

In an embodiment, the molar ratio of sialic acid/polypeptide dimer in the polypeptide dimer having a high content of sialic acid may be at least 8, at least 9, at least 10, at least 11, at least 12, at least 13, at least 14, at least 15, at least 16, at least 17, at least 18, at least 19, at least 20, or at least 21. In addition, the molar ratio of sialic acid/polypeptide dimer in the polypeptide dimer having a high content of sialic acid may be 8 to 30 or 12 to 25. In addition, the molar ratio of sialic acid/polypeptide dimer in the polypeptide dimer having a high content of sialic acid may be 10 to 25, 11 to 24 or 12 to 23. Also, the molar ratio of sialic acid/polypeptide dimer in the polypeptide dimer having a high content of sialic acid may be 13 to 22, 14 to 22, 15 to 22, 16 to 22, 17 to 22, 18 to 22, or 19 to 22. Here, the sialic acid may be N-aceytylneuraminic acid.

In addition, the sialic acid can bind to 8 positions on a monomer comprising an extracellular domain (FcεRIα-ECD) of an alpha subunit of an IgE Fc receptor and an Fc region. In this case, the sialic acid can bind to at least 4 or more of the above positions. Specifically, the sialic acid can bind to 4, 5, 6, 7 or 8 positions on the monomer.

As described above, the polypeptide dimer having a high content of sialic acid provided by the present invention may be in a form in which two monomers are bound to each other and each monomer is obtained by binding between an extracellular domain of an alpha subunit of an IgE Fc receptor and a modified Fc region. The polypeptide dimer having a high content of sialic acid may be in a form in which the same two monomers are bound to each other by cysteine located at a hinge site. In addition, the polypeptide dimer having a high content of sialic acid may be in a form in which two different monomers are bound to each other.

In this case, each polypeptide monomer may comprise sialic acid at the same position, but may comprise sialic acid at a different position. In addition, if the molar ratio of sialic acid/polypeptide dimer is 8 or more, each monomer constituting the dimer may have a different molar ratio of sialic acid/polypeptide.

In addition, the polypeptide dimer may contain two monomers different from each other. Specifically, it may be in a form in which one monomer may contains the extracellular domain of the alpha subunit of the IgE Fc receptor, and the other monomer contains a fragment of the extracellular domain of the alpha subunit of the IgE Fc receptor. Here, an embodiment of the monomer may be composed of the amino acid sequence represented by SEQ ID NO: 20, SEQ ID NO: 21, or SEQ ID NO: 22.

In addition, the polypeptide dimer having a high content of sialic acid provided by the present invention exhibits a binding affinity to IgE which is 10- to 100-fold, 20- to 90-fold, 20- to 70-fold, 30- to 70-fold, or 40- to 70-fold higher than omalizumab, an anti-IgE antibody, and may preferably exhibit a binding affinity to IgE which is about 70-fold higher than omalizumab.

Another aspect of the present invention provides a pharmaceutical composition for preventing or treating allergic diseases, comprising the polypeptide dimer having a high content of sialic acid.

The polypeptide dimer is the same as described above. In particular, the pharmaceutical composition may be characterized by being for subcutaneous injection. It was confirmed that a polypeptide dimer having a high content of sialic acid is effective in treating and/or preventing allergic diseases compared to a polypeptide dimer having a low content of sialic acid upon subcutaneous injection.

As used herein, the term "allergic disease" means a pathological symptom caused by an allergic reaction mediated by mast cell activation such as mast cell degranulation. For example, such allergic diseases may be the one selected from the group consisting of food allergy, atopic dermatitis, asthma, allergic rhinitis, allergic conjunctivitis, allergic dermatitis, chronic idiopathic urticaria and allergic contact dermatitis, but are not limited thereto. In particular, the allergic diseases may be IgE-mediated.

In the pharmaceutical composition, the polypeptide dimer may be contained in any amount (effective amount) depending on use, formulation, blending purpose, and the like, as long as the polypeptide dimer can exhibit anti-allergic activity. A typical effective amount of the polypeptide dimer will be determined within a range of 0.001% by weight to 20.0% by weight based on a total weight of the composition. Here, the effective amount refers to an amount which is capable of inducing an anti-allergic effect. Such an effective amount can be determined by those ordinarily skilled in the art.

The pharmaceutical composition may further contain a pharmaceutically acceptable carrier. Specifically, the pharmaceutical composition contains a pharmaceutically acceptable carrier, and may be made into an oral or parenteral formulation depending on a route of administration by a conventional method known in the art.

In a case where the pharmaceutical composition of the present invention is made into an oral formulation, the pharmaceutical composition may be made into formulations such as powders, granules, tablets, pills, sugar coating tablets, capsules, liquids, gels, syrups, suspensions, and wafers, together with suitable carriers, in accordance with methods known in the art. Here, examples of suitable pharmaceutically acceptable carriers can include sugars such as lactose, glucose, sucrose, dextrose, sorbitol, mannitol, and xylitol, starches such as corn starch, potato starch, and wheat starch, celluloses such as cellulose, methylcellulose, ethylcellulose, sodium carboxymethyl cellulose, and hydroxypropylmethyl cellulose, polyvinyl pyrrolidone, water, methylhydroxybenzoate, propylhydroxybenzoate, magnesium stearate, mineral oil, malt, gelatin, talc, polyol, vegetable oil, and the like. In a case of being made into preparations, the preparations can be carried out, as necessary, by including diluents and/or excipients such as a filler, an extender, a binder, a wetting agent, a disintegrant, and a surfactant.

In a case where the pharmaceutical composition of the present invention is made into a parenteral formulation, the pharmaceutical composition may be made into preparations in the form of injections, transdermal drugs, nasal inhalers, and suppositories, together with suitable carriers, in accordance with methods known in the art. In a case of being prepared into injections, sterilized water, ethanol, polyol such as glycerol and propylene glycol, or a mixture thereof may be used as a suitable carrier. For the carrier, isotonic solutions such as Ringer's solution, phosphate buffered saline (PBS) containing triethanolamine, sterile water for injection, and 5% dextrose, and the like may be preferably used.

Preparation of the pharmaceutical composition is known in the art and specifically, reference can be made to Remington's Pharmaceutical Sciences (19th ed., 1995) and the like.

A preferable daily dosage of the pharmaceutical composition of the present invention is ranged from 0.01 μg/kg to 10 g/kg, and preferably from 0.01 mg/kg to 1 g/kg, depending on the patient's condition, body weight, sex, age, disease severity, or route of administration. The pharmaceutical composition may be administered once a day or several times a day when the dosage is high.

The subject to which the composition of the present invention can be applied (prescribed) is a mammal and may be, for example, a human, a dog and a cat, with a human being particularly preferred but not limited thereto. The pharmaceutical composition may further comprise any compound or natural extract, on which safety has already been verified and which is known to have anti-allergic activity, for the purpose of raising and reinforcing the anti-allergic activity.

Figure 13:
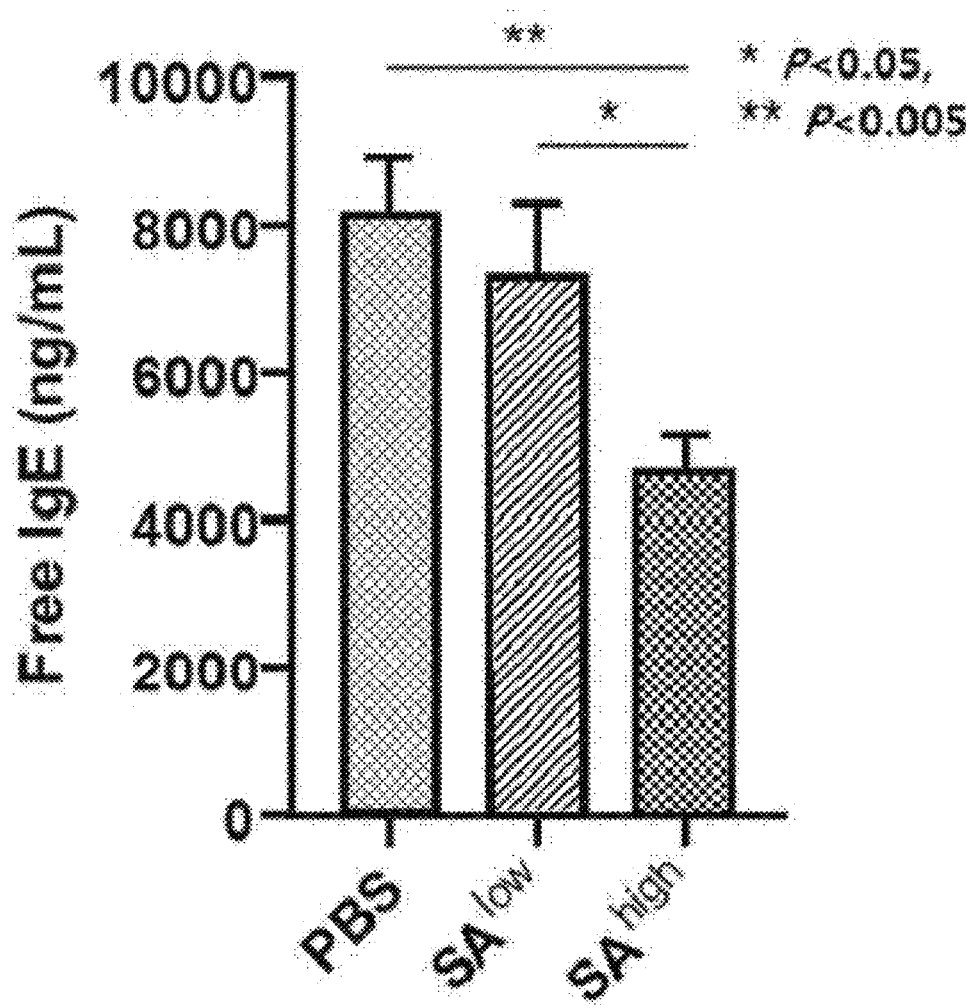
FIG. 13 is a view confirming the anti-allergic effect of a polypeptide dimer according to an embodiment of the present invention ($SA^{low}$ and $SA^{high}$) by measuring the IgE concentration in the blood in a food allergy model.
Figure 14:
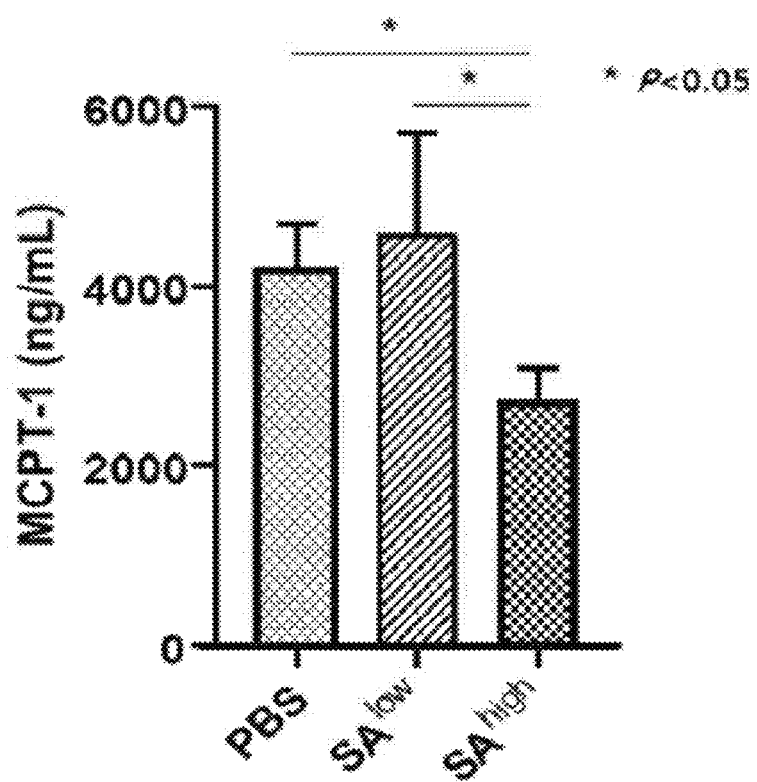
FIG. 14 is a view confirming the anti-allergic effect of a polypeptide dimer according to one embodiment ($SA^{low}$ and $SA^{high}$) by measuring the MCPT-1 concentration in the blood in a food allergy model.

The present inventors studied to develop a safe and effective therapeutic agent for allergic diseases. As a result, it was confirmed that a polypeptide dimer having a high content of sialic acid has excellent binding affinity with IgE compared to a polypeptide dimer having a low content of sialic acid (Table 3). In addition, it was confirmed that when a polypeptide dimer having a high content of sialic acid is administered subcutaneously to a subject suffering from an allergic disease, the concentration of IgE and MCPT-1 in the blood is effectively reduced compared to a polypeptide dimer having a low content of sialic acid, and the effect persists even after a predetermined time has passed (FIGS. 13 and 14).

Accordingly, another aspect of the present invention provides a transdermal patch comprising the pharmaceutical composition. In addition, another aspect of the present invention provides a topical patch comprising the pharmaceutical composition.

Another aspect of the present invention provides a food composition for ameliorating or alleviating allergic symptom, comprising the polypeptide dimer having a high content of sialic acid.

The polypeptide dimer having a high content of sialic acid is the same as described above. In addition, the polypeptide dimer having a high content of sialic acid may be bound to appropriate delivery means for efficient delivery into the intestine.

In addition, the food composition may be prepared in any form and may be, for example, prepared in the form of beverages such as tea, juice, carbonated beverage, and ionic beverage, processed dairy products such as milk and yogurt, health functional food preparations such as tablets, capsules, pills, granules, liquids, powders, flakes, pastes, syrups, gels, jellies, and bars, or the like.

The food composition may fall within any product category in legal or functional classification as long as the food composition complies with the enforcement regulations at the time of being manufactured and distributed. For example, the food composition may be a health functional food according to the Health Functional Foods Act, or may fall within confectioneries, beans, teas, beverages, special-purpose foods, or the like according to each food type in the Food Code of Food Sanitation Act (standards and specifications for food, notified by Food and Drug Administration). With regard to other food additives that may be contained in the food composition of the present invention, reference can be made to the Food Code or the Food Additive Code according to the Food Sanitation Act.

Another aspect of the present invention provides a method for treating or preventing allergic diseases, comprising a step of administering to a subject the polypeptide dimer having a high content of sialic acid. The polypeptide dimer having a high content of sialic acid is the same as described above.

The subject may be a mammal, preferably, a human, a dog and a cat. Here, administration may be achieved orally or parenterally. Here, parenteral administration may be performed by methods such as subcutaneous administration, intravenous administration, mucosal administration, and muscular administration.

The allergic diseases may be the one selected from the group consisting of food allergy, atopic dermatitis, asthma, allergic rhinitis, allergic conjunctivitis, allergic dermatitis, chronic idiopathic urticaria and allergic contact dermatitis.

Another aspect of the present invention provides a use of the polypeptide dimer having a high content of sialic acid for preventing or treating allergic diseases.

Hereinafter, the present invention will be described in more detail with reference to the following examples. However, the following examples are intended to merely illustrate the present invention, and the scope of the present invention is not limited only thereto.

Example 1. Preparation of Polypeptide Containing FcεRIα-ECD and Fc Region

A C-terminal modified polypeptide of the extracellular domain (FcεRIα-ECD) of the alpha subunit of the IgE Fc receptor was prepared according to the method disclosed in U.S. Pat. No. 7,867,491.

First, in order to express a protein (FcεRIαECD-Fc1), a protein (FcεRIαECD-Fc2), and a protein (FcεR1αECD-Fc3), in which the extracellular domain of the α-chain of FcεRI having the amino acid sequence of SEQ ID NO: 1 and the modified immunoglobulin Fc of SEQ ID NO: 2 are linked via a hinge of SEQ ID NO: 19, a hinge of SEQ ID NO: 3, and a hinge of SEQ ID NO: 4, respectively, cassettes obtained by linking the gene encoding each protein were cloned into the pAD15 vectors (Genexin, Inc.) to construct FcεRIαECD-Fc protein expression vectors. Then, each of the expression vectors was transduced into CHO DG44 cells (from Dr. Chasm, Columbia University, USA).

Here, at the time of being transduced into the cell line, an expression vector obtained by cloning an α-2,6-sialic acid transferase gene into the pCI Hygro vector (Invitrogen) was simultaneously transduced to separately prepare cell lines which are capable of expressing FcεRIαECD-Fc2ST and FcεRIαECD-Fc3ST proteins to which sialic acid is added.

As a primary screening procedure, HT selection was carried out using 5-hydroxytryptamine (HT)-free 10% dFBS medium (Gibco, USA, 30067-334), MEMα medium (Gibco, 12561, USA, Cat No. 12561-049), and HT+ medium (Gibco, USA, 11067-030). Then, methotrexate (MTX) amplification was performed using HT-selected clones to amplify productivity using the dihydrofolate reductase (DHFR)-system.

After completion of the MTX amplification, subculture was carried out about 1 to 5 times for cell stabilization for the purpose of evaluation of productivity. Thereafter, unit productivity evaluation of the MTX-amplified cells was performed. The results are shown in Table 1 below.

TABLE 1

| Version | Media | MTX concen- tration | Productivity 3-day culture ug/mL | ug/$10^6$ cells | Batch culture (mg/ml) |
|---|---|---|---|---|---|
| FcεRIαECD-Fc2 | Ex- cellDHFR | 500 nM | 37.23 | 20.9 | 225 |
| FcεRIαECD- Fc2 + a2,6-ST | | 100 nM | 45.4 | 25.1 | 338.2 |
| FcεRIαECD-Fc3 | | 2 uM | 27.0 | 16.9 | 180.4 |
| FcεRIαECD- Fc3 + a2,6-ST | | 1 uM | 17.5 | 10.2 | 101.7 |

As shown in Table 1, the FcεRIαECD-Fc3 cell line exhibited productivity of 16.9 μg/$10^6$ cells after the methotrexate amplification at 2 uM. On the other hand, the FcεRIαECD-Fc3 cell line (FcεRIαECD-Fc3ST) co-transduced with 2,6-sialic acid transferase exhibited productivity of 10.2 μg/10⁶ cells after the methotrexate amplification at 1 uM. In addition, the FcεRIαECD-Fc2 cell line exhibited productivity of 20.9 μg/10⁶ cells under the methotrexate amplification condition at 0.5 uM. In addition, the FcεRIαECD-Fc2 cell line (FcεRIαECD-Fc2ST) co-transduced with 2,6-sialic acid transferase exhibited productivity of 25.1 μg/10⁶ cells after the methotrexate amplification at 0.1 uM. That is, it was identified that the FcεRIαECD-Fc2 cell line co-transduced with 2,6-sialic acid transferase, which had been selected under the methotrexate amplification condition at 0.1 uM, exhibits the most excellent productivity.

The polypeptide (FcεRIαECD-Fc) produced from the FcεRIαECD-Fc2 cell line is referred to as "FcεRIαECD-Fc2," and the polypeptide produced from the FcεRIαECD-Fc2+a2,6-ST cell line is referred to as "FcεRIαECD-Fc2ST". In addition, the polypeptide produced from the FcεRIαECD-Fc3 cell line is referred to as "FcεRIαECD-Fc3," and the polypeptide produced from the FcεRIαECD-Fc3+a2,6-ST cell line is referred to as "FcεRIαECD-Fc3ST".

Example 2. Confirmation of Purification and Purity of Polypeptide (FcεRIα ECD-Fc)

Among the cell lines selected in Example 1 above, i) FcεRIαECD-Fc3 cell line, ii) FcεRIαECD-Fc3+a2,6-ST cell line, and iii) FcεRIαECD-Fc2+a2,6-ST cell line were cultured at a 60 ml scale by a batch culture method. The resulting cultures were purified using a Protein-A affinity column to obtain FcεRIαECD-Fc, and then the purified FcεRIα ECD-Fc were subjected to SE-HPLC(Size-Exclusion High performance liquid chromatography) and SDS-PAGE to identify purity of the polypeptide.

Specifically, SDS-PAGE was performed under a non-reducing condition. In the non-reducing condition, each purified polypeptide was mixed with a non-reducing sample buffer, and then electrophoresis was performed for 30 minutes in a Mini-Protean TGX™ gels (Bio-Rad) in a TGS (Tris Glycine SDS) buffer under a 200V condition. After electrophoresis, a protein was stained with a Coomassie Brilliant Blue solution. The results are shown in Table 2 and FIG. 1 below:

TABLE 2

| Lane # | Sample | Purification | Purity (SE-HPLC) | Sample condition | |
|---|---|---|---|---|---|
| M | Protein standard | One-step | — | — | — |
| 1 | FcεRIαECD-Fc3 | (Protein-A | 94.5% | — | Non-reducing |
| 2 | FcεRIαECD-Fc3ST | affinity | 93.7% | | |
| 3 | FcεRIαECD-Fc2ST | column) | 93.2% | | |
| 4 | FcεRIαECD-Fc3 | Purification | 94.5% | Freezing/Thawing test | |
| 5 | FcεRIαECD-Fc3ST | | 93.7% | | |
| 6 | FcεRIαECD-Fc2ST | | 93.2% | | |

As shown in Table 2 above, it was confirmed that the purity of each polypeptide purified by the SE-HPLC method was 93% or more. It was confirmed that impurities such as a truncated form did not appear in a non-reducing condition, and in particular, the purity was 93% or more and there were no impurities even after the thawing/freezing process.

Experimental Example 1. Confirmation of Dimer Formation of Polypeptide (FcεRIα ECD-Fc)

Among the cell lines selected in Example 1 above, i) FcεRIαECD-Fc3 cell line, ii) FcεRIαECD-Fc3+a2,6-ST cell line, and iii) FcεRIαECD-Fc2+a2,6-ST cell line were cultured at a 60 ml scale by a batch culture method. Thereafter, SE-HPLC and SDS-PAGE were performed on the purified product obtained from the purification of polypeptide using the culture supernatant and Protein-A affinity column. In this case, they were performed on the culture supernatant and the purified product under a non-reducing condition and a reducing condition, respectively.

The non-reducing condition was performed in the same manner as in Example 2. On the other hand, in a reducing condition, each purified polypeptide was mixed with a reducing sample buffer comprising 2-mercaptoethanol, and then denatured at a temperature of 100° C. for 5 minutes. Thereafter, electrophoresis was performed for 30 minutes under a 200V condition using a TGS buffer in Mini-Protean TGX™ gels (Bio-Rad). After electrophoresis, a protein was stained with a Coomassie Brilliant Blue solution.

Figure 2:
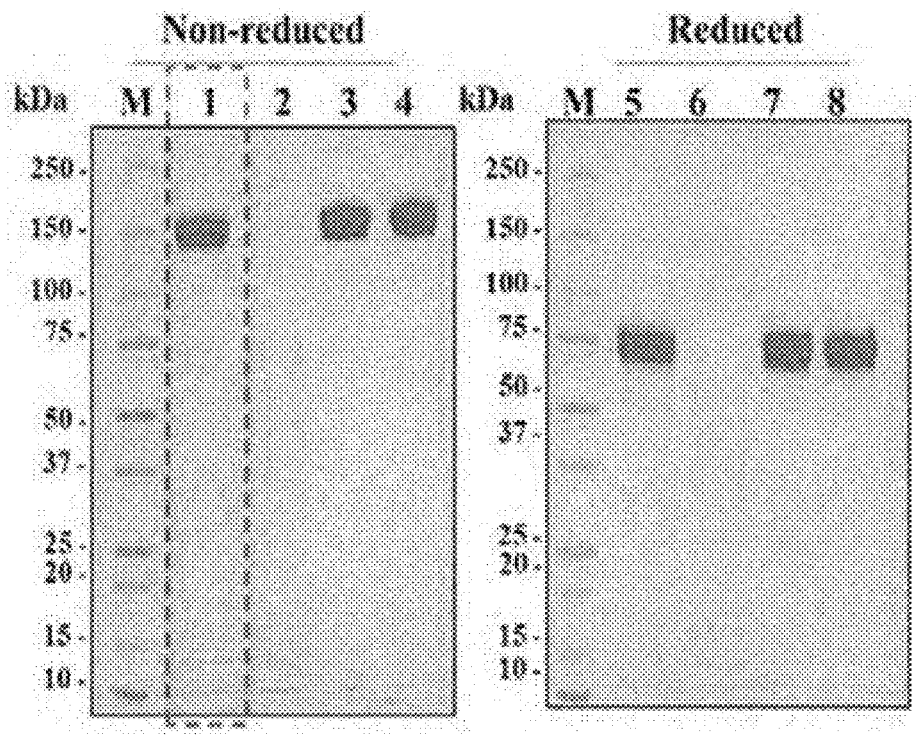
FIG. 2 is a view showing SDS-PAGE results for a non-reduced form and a reduced form of a polypeptide dimer according to one embodiment.

As a result, a polypeptide having a size of about 150 kDa was detected under a non-reducing condition, and a polypeptide having a size of about 75 kDa was detected under a reducing condition. Through this, it was confirmed that the polypeptide forms a dimer (FIG. 2). In particular, it was confirmed that the purity of a polypeptide dimer is high even in the culture supernatant corresponding to the input, and no polypeptide was detected in the sample (FT; Flow Through) obtained by passing the culture supernatant through an affinity column, but a polypeptide was detected in the eluted sample. In addition, no significant difference was observed even when the sample (Elute N) that was immediately neutralized with 1 M Tris buffer (pH 9.0) due to the low pH of the eluted sample was compared with the sample (Elute) that was not neutralized (FIG. 2).

In addition, it was identified that not only polypeptides with very high purity (98% or higher) are purified but also polypeptides are expressed with very high purity even in the culture supernatant. This indicates that process development steps can be simplified in developing the polypeptides, which had been expressed in the cell lines in question, into a medical product, and as a result, it is highly likely for the development cost of the medical product to be remarkably decreased.

Experimental Example 2. Confirmation of Binding Affinity of Polypeptide Dimer to IgE A binding affinity to IgE was comparatively measured for the purified products obtained by purifying the polypeptides which had been produced in Example 1, i) FcεRIαECD-Fc2, ii) FcεRIαECD-Fc2ST, iii) FcεRIαECD-Fc3, and iv) FcεRIαECD-Fc3ST, through the method of Example 2 above, and the commercially available anti-IgE antibody, omalizumab (trade name: Xolair).

Specifically, the binding affinity to IgE was measured by coating IgE on the channel of the Protein GLC sensor chip (Bio-Rad Laboratories, Inc., Cat #176-5011), and causing omalizumab or each FcεR1αECD-Fc protein at various concentrations to flow at a rate of 30 μL per minute. Here, the experiments were conducted by identifying zero base using 25 mM NaOH as a regeneration buffer, and then repeating the above steps. Thereafter, a binding curve was identified using a protein binding analyzer (ProteOn XPR36, Bio-Rad Laboratories, Inc., USA). The results are shown in Table 3.

TABLE 3

| Samples items Drug type | | FcεRIα ECD-Fc Fc fusion protein | | Omalizumab Anti-IgE Ab | Remarks |
|---|---|---|---|---|---|
| Binding affinity | ka (Association rate) | Fc2 | $2.14 \times 10^5$ | $4.05 \times 10^5$ | 1.9-fold weaker than omalizumab |
| | | Fc2ST | $2.64 \times 10^5$ | | 1.5-fold weaker than omalizumab |
| | | Fc3 | $1.98 \times 10^5$ | | 2.0-fold weaker than omalizumab |
| | | Fc3ST | $2.40 \times 10^5$ | | 1.7-fold weaker than omalizumab |
| | kd (Dissociation rate) | Fc2 | $8.29 \times 10^{-5}$ | $6.02 \times 10^{-3}$ | 73-fold better than omalizumab |
| | | Fc2ST | $5.69 \times 10^{-5}$ | | 106-fold better than omalizumab |
| | | Fc3 | $1.33 \times 10^{-4}$ | | 45-fold better than omalizumab |
| | | Fc3ST | $1.49 \times 10^{-4}$ | | 40-fold better than omalizumab |
| | KD (kd/ka) | Fc2 | $3.88 \times 10^{-10}$ | $1.49 \times 10^{-8}$ | 38-fold better than omalizumab |
| | | Fc2ST | $2.16 \times 10^{-10}$ | | 69-fold better than omalizumab |
| | | Fc3 | $6.72 \times 10^{-10}$ | | 22-fold better than omalizumab |
| | | Fc3ST | $6.21 \times 10^{-10}$ | | 24-fold better than omalizumab |

As shown in Table 3, the association rate (ka) value of the polypeptide dimer according to an embodiment of the present invention and IgE was measured to be 1.5- to 2.0-fold lower than that of omalizumab. That is, it was found that a binding affinity thereof to substances other than IgE is 1.5- to 2.0-fold lower than that of omalizumab. In addition, the dissociation rate (kd) value of the polypeptide dimer according to an embodiment of the present invention was measured to be 40- to 106-fold higher than that of omalizumab. As a result, it was confirmed that the polypeptide dimer according to an embodiment of the present invention has an equilibrium dissociation constant (KD<kd/ka>) value which is 22- to 69-fold higher than omalizumab. From this, it was identified that the polypeptide dimer according to an embodiment of the present invention has a remarkably increased binding affinity to IgE as compared with omalizumab. In particular, it was identified that the polypeptide dimer to which sialic acid is added (FcεRIαECD-Fc2ST) exhibits the highest IgE-binding affinity which is 69-fold higher than omalizumab.

Figure 3:
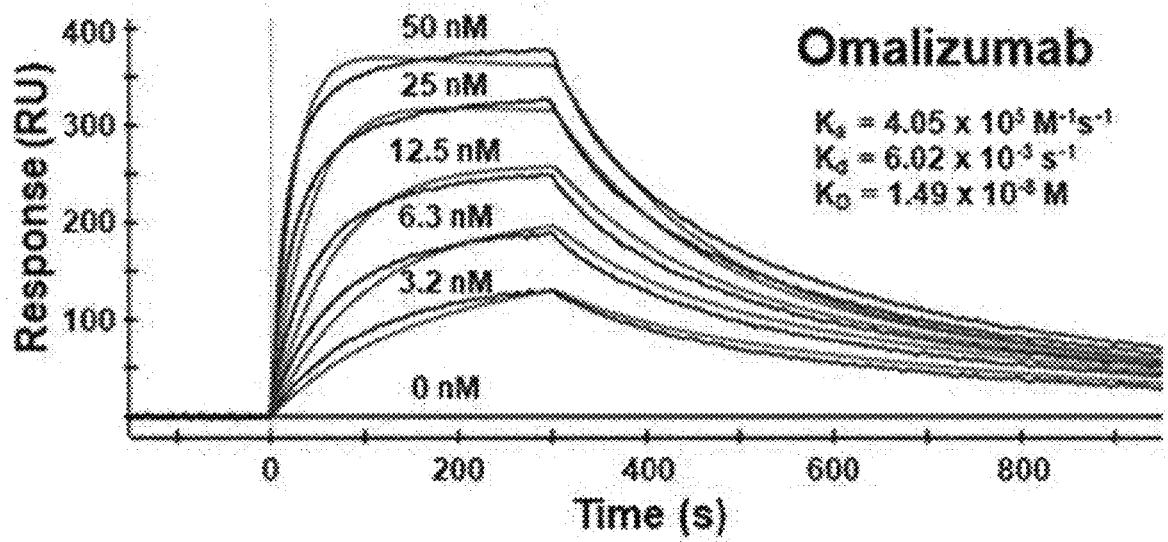
FIG. 3 is a view showing a binding affinity of omalizumab to IgE.
Figure 4:
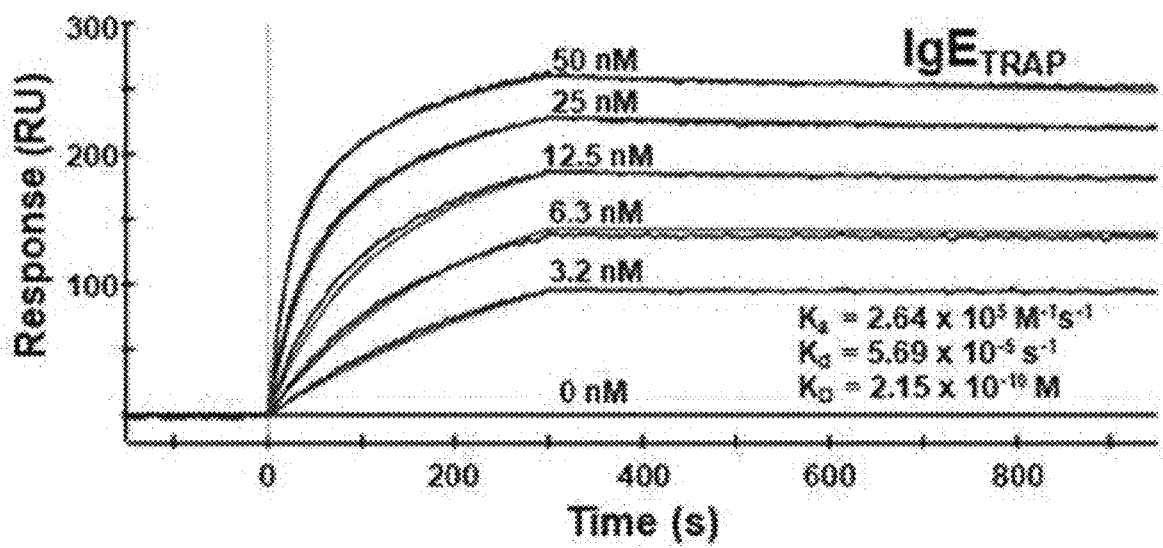
FIG. 4 is a view showing a binding affinity of the polypeptide dimer ($IgE_{TRAP}$) according to an embodiment of the present invention to IgE.
Figure 5A:
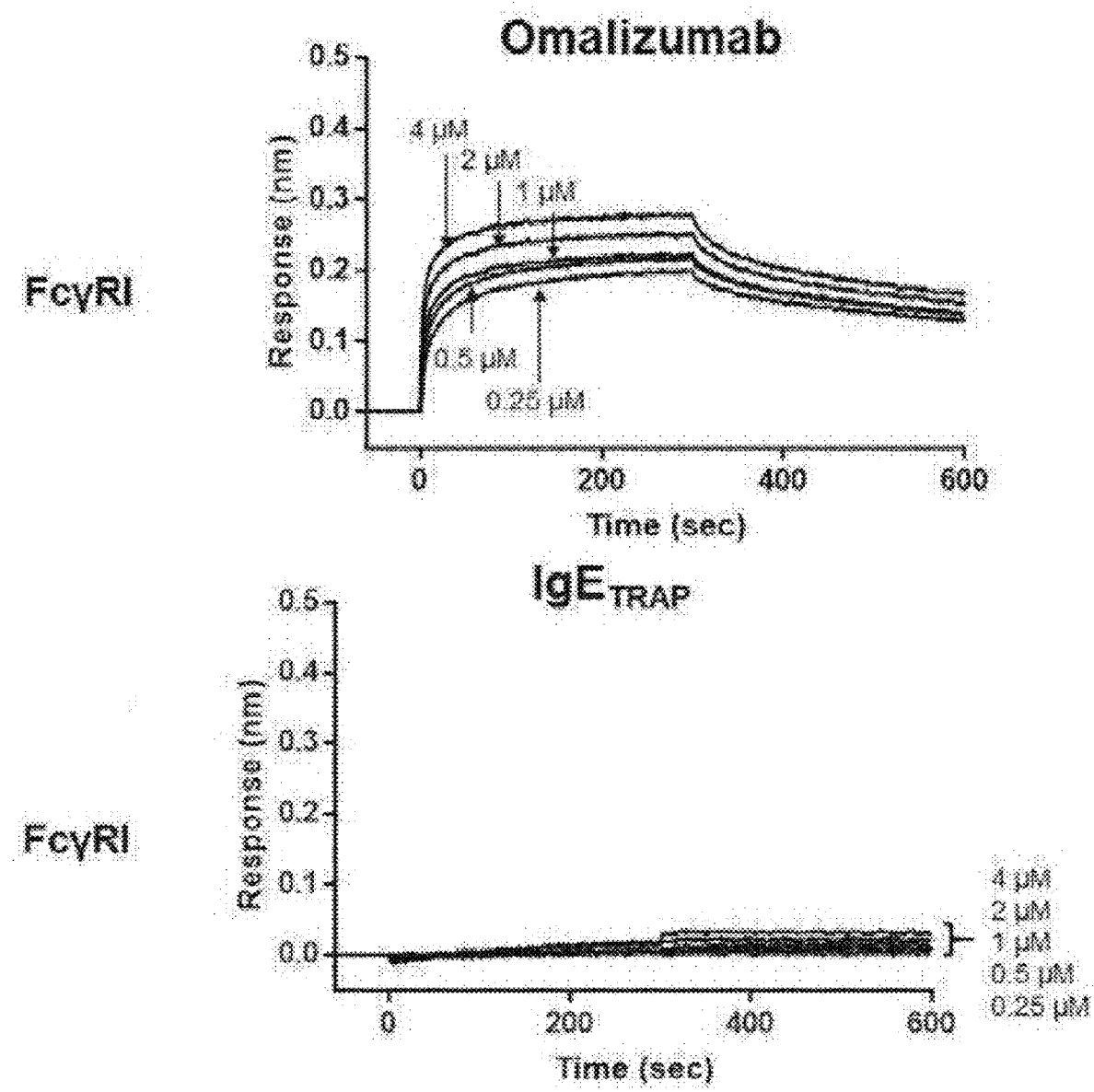
FIG. 5a is a view showing a binding affinity of the polypeptide dimer ($IgE_{TRAP}$) according to an embodiment of the present invention or omalizumab to IgG Fc gamma receptor I (FcγRI).
Figure 5B:
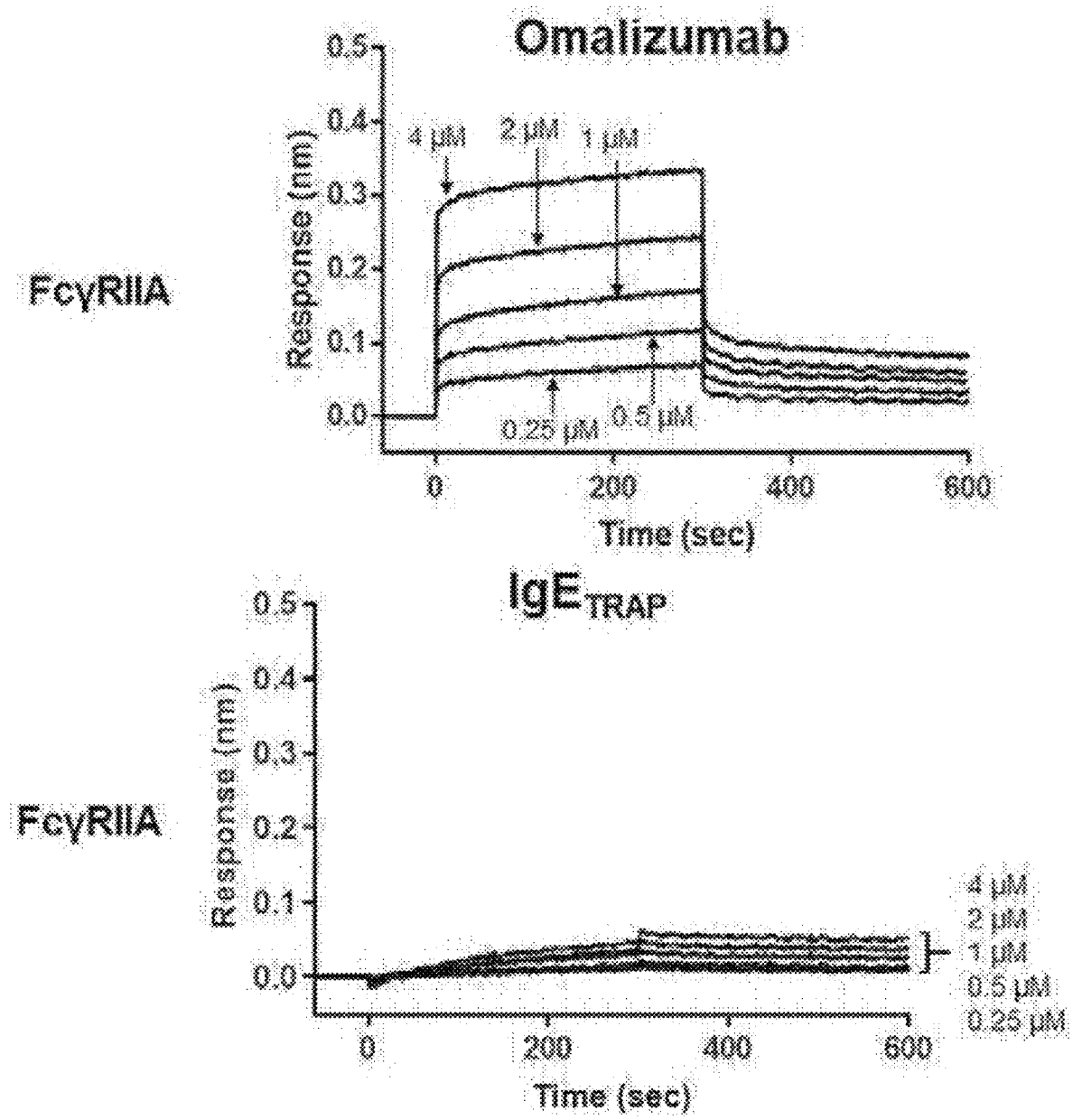
FIG. 5b is a view showing a binding affinity of the polypeptide dimer ($IgE_{TRAP}$) according to an embodiment of the present invention or omalizumab to IgG Fc gamma receptor IIA (FcγRIIA).
Figure 5C:
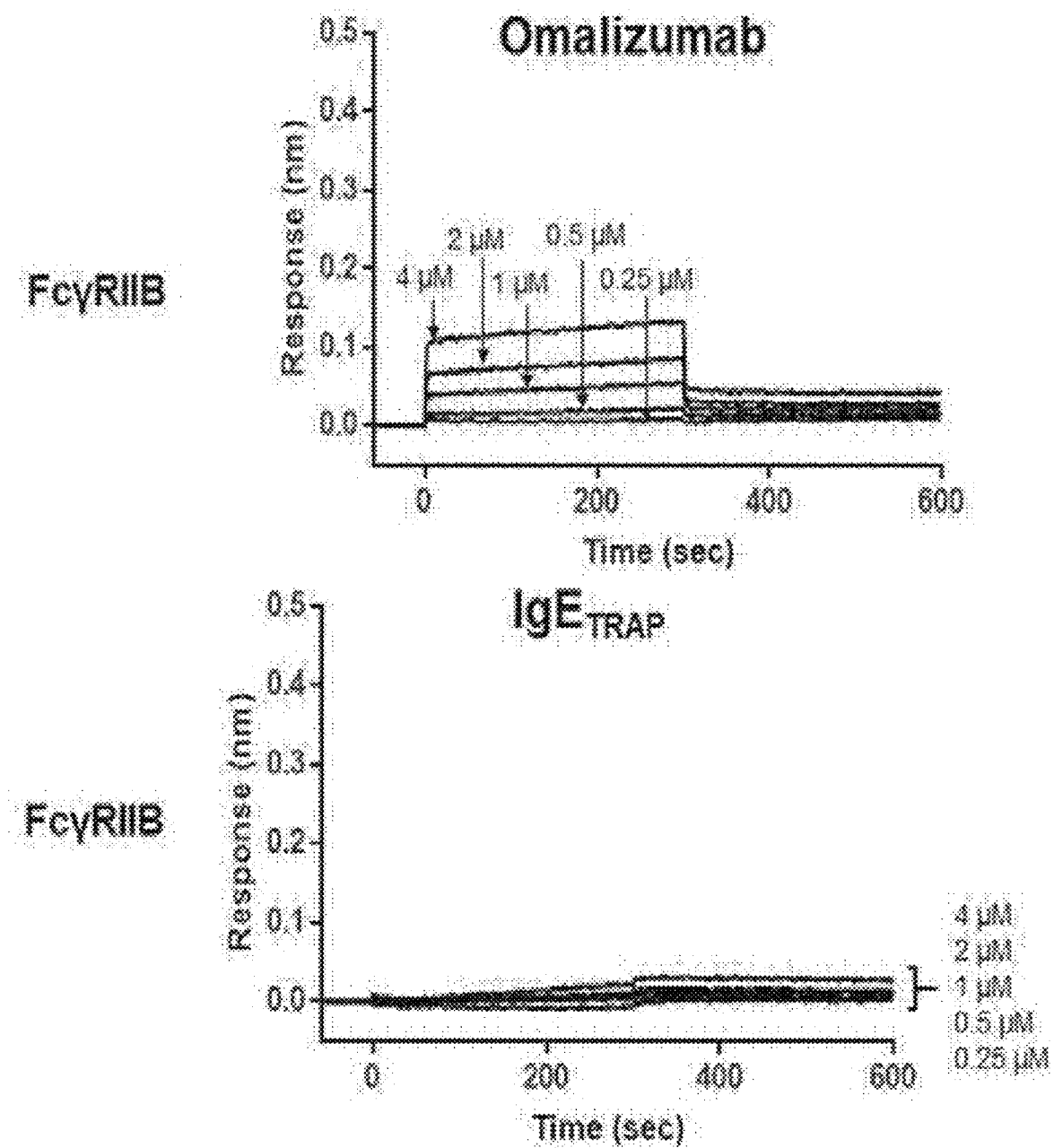
FIG. 5c is a view showing a binding affinity of the polypeptide dimer ($IgE_{TRAP}$) according to an embodiment of the present invention or omalizumab to IgG Fc gamma receptor IIB (FcγRIIB).
Figure 5D:
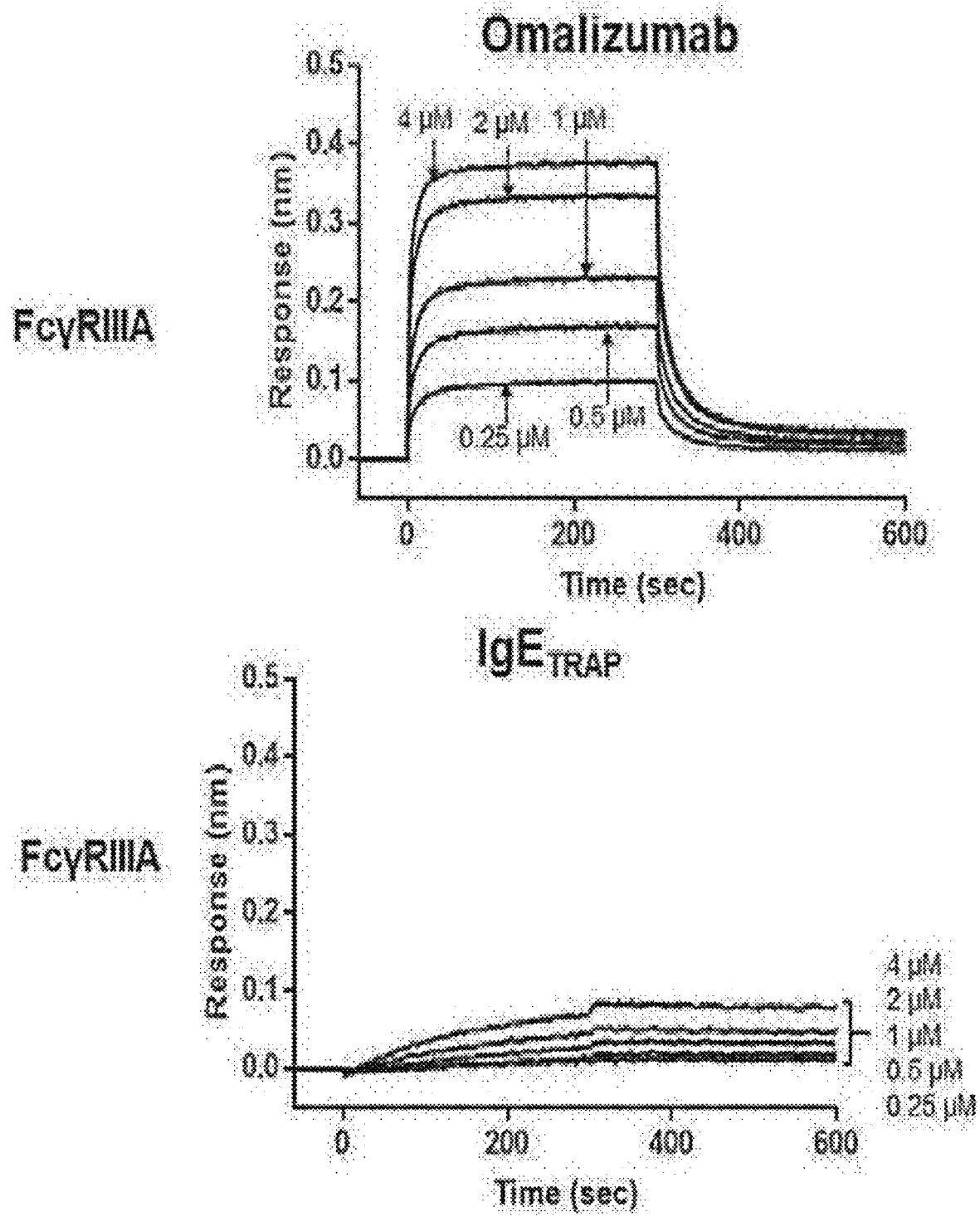
FIG. 5d is a view showing a binding affinity of the polypeptide dimer ($IgE_{TRAP}$) according to an embodiment of the present invention or omalizumab to IgG Fc gamma receptor IIIA (FcγRIIIA).
Figure 5E:
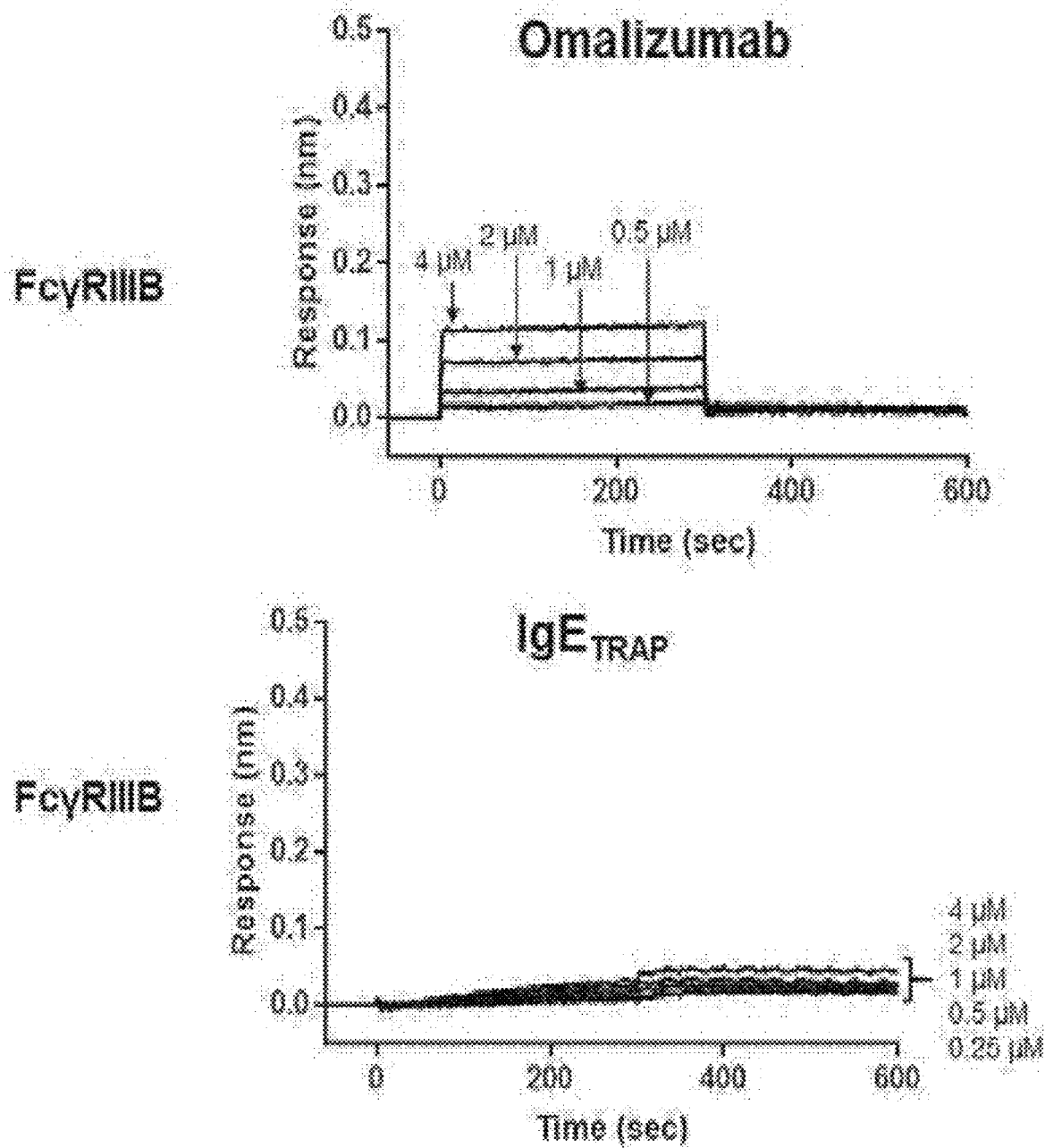
FIG. 5e is a view showing a binding affinity of the polypeptide dimer ($IgE_{TRAP}$) according to an embodiment of the present invention or omalizumab to IgG Fc gamma receptor IIIB (FcγRIIIB).

In addition, as shown in FIGS. 3 and 4, it was confirmed that omalizumab loses its binding to IgE when a certain period of time has passed after the binding, whereas the polypeptide dimer according to an embodiment of the present invention (FcεRIαECD-Fc2ST, IgE$_{TRAP}$) is not separated from IgE once it binds to IgE. That is, it was confirmed that the polypeptide dimer according to an embodiment of the present invention is not easily separated from IgE, and has a much better ability to maintain its bound state than omalizumab.

Experimental Example 3. Confirmation of Binding Affinity of Polypeptide Dimer to IgG Receptors The binding affinity of a polypeptide dimer according to an embodiment of the present invention (FcεRIαECD-Fc2ST, IgE$_{TRAP}$) or omalizumab (Xolair) to Fc gamma receptors of IgG was confirmed using Octet RED384 system (Pall ForteBio, CA, USA).

Figure 6:
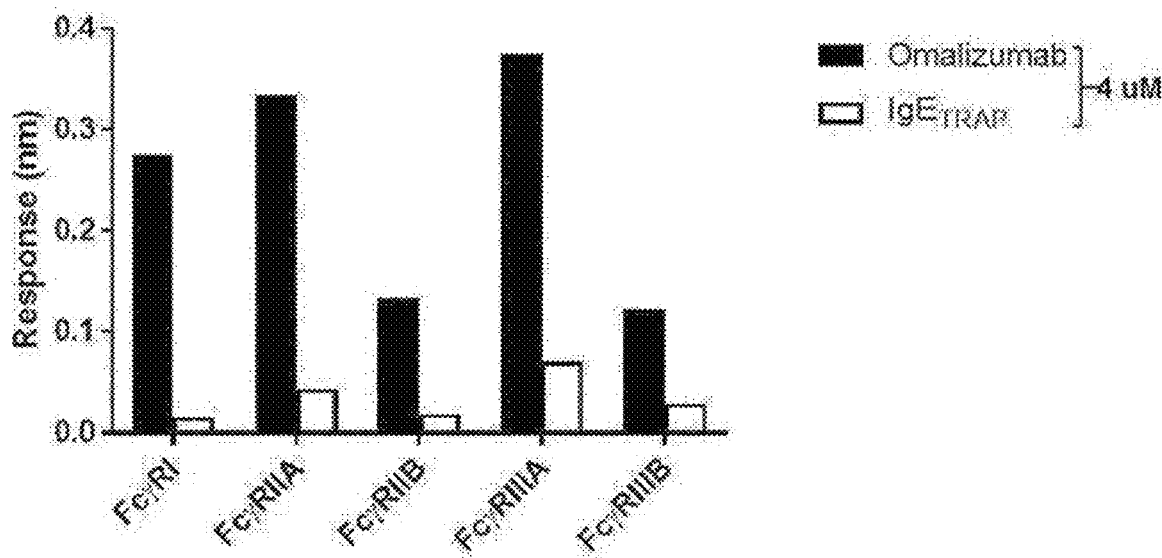
FIG. 6 is a graph obtained by quantifying a binding affinity between the polypeptide dimer ($IgE_{TRAP}$) according to an embodiment of the present invention or omalizumab and IgG Fc gamma receptors.

Specifically, FcγRI, FcγRIIA, FcγRIIB, FcγRIIIA, and FcγRIIIB recombinant proteins (R & D Systems Inc., 5 μg/ml) which are Fc gamma receptors were immobilized in 300 mM acetate buffer (pH 5) on the activated AR2G biosensor. As a running buffer, PBS containing 0.1% Tween-20 and 1% bovine serum was used. All measurements were carried out at 30° C. with a sample plate shaker at a rate of 1,000 rpm. The results are shown in FIGS. 5a to 5e, and binding affinity of omalizumab and the polypeptide dimer to the IgG Fc gamma receptors are quantified and shown in FIG. 6.

As a result, it was confirmed that omalizumab showed a high binding affinity to Fc gamma receptors of IgG, whereas the polypeptide dimer had a significantly low binding affinity to Fc gamma receptors of IgG. Through this, it was confirmed that the polypeptide dimer does not bind with Fc gamma receptors of IgG.

Experimental Example 4. Confirmation of Activity of Polypeptide Dimer Through Beta-Hexosaminidase Assay in Mouse Bone Marrow-Derived Mast Cells Beta-hexosaminidase assay was performed for in vitro activity analysis of the polypeptide dimer according to an embodiment of the present invention.

Specifically, the polypeptide dimer (FcεRIαECD-Fc2) according to an embodiment of the present invention was mixed, at each concentration, with IgE (1 μg/mL), and incubated at 20° C. for 30 minutes to prepare samples. Mouse bone marrow-derived mast cells in culture for mast cell activation were washed with Hank's balanced salt solution (HBSS) buffer to remove the medium, the number of cells was measured, and then $5 \times 10^5$ cells were refloated into 40 μL of HBSS buffer.

50 μL of the sample thus prepared was added to activated mast cells. Then, the resultant was incubated in a 5% $CO_2$ incubator at 37° C. for 30 minutes. Subsequently, after the addition of each 10 μL of DNP (2,4-dinitrophenol, 100 ng/mL), which is a foreign antigen, incubation was performed again at 37° C. for 30 minutes in 5% $CO_2$, and then 30 μL of the supernatant was separated.

30 μL of the separated supernatant and 30 μL of the substrate (4-nitrophenyl N-acetyl-β-D-glucosaminide, 5.84 mM) were mixed well, and then incubated at 37° C. for 20 minutes in 5% $CO_2$. Then, 140 μL of 0.1 M sodium carbonate buffer (pH 10) as a stop solution was added to terminate the reaction. Thereafter, absorbance at 405 nm was measured to identify a secretion amount of β-hexosaminidase secreted by the foreign antigen in the activated mast cells. The results are shown in FIG. 7.

Figure 7:
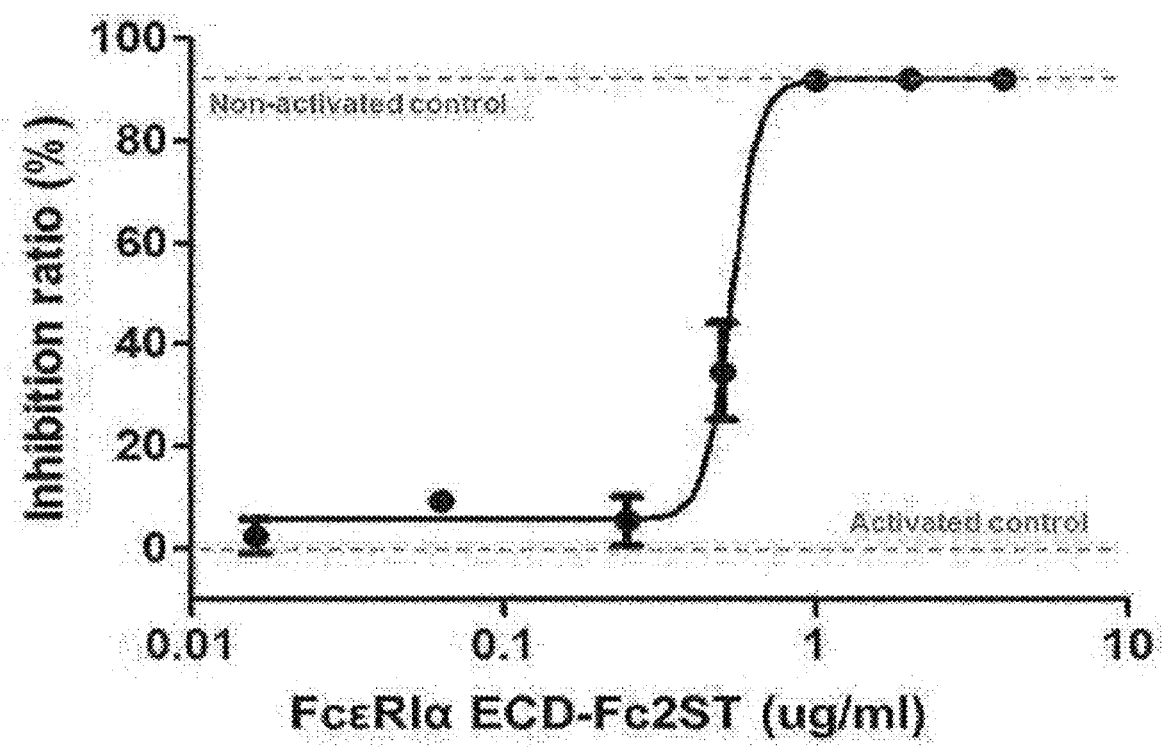
FIG. 7 is a view showing a degree of binding with IgE depending on the concentration of a polypeptide dimer according to an embodiment of the present invention.

As shown in FIG. 7, it was confirmed that the activity of IgE is considerably inhibited from the case in which the concentration of IgE and the polypeptide dimer of the present invention is 1:1. That is, it was confirmed that the polypeptide dimer according to an embodiment of the present invention reacts even when the concentration thereof is the same as that of IgE.

Experimental Example 5. Comparison of Activity of Polypeptide Dimer and Human Anti-IgE Antibody Using β-Hexosaminidase Assay in Human FcεRI-Expressing Mouse Bone Marrow-Derived Mast Cells In order to compare the activity of the polypeptide dimer according to an embodiment of the present invention (FcεRIαECD-Fc2ST, IgE$_{TRAP}$) and Xolair (omalizumab), which is a human anti-IgE antibody, a beta-hexosaminidase analysis was performed.

The respective polypeptide dimers and Xolair were prepared at each concentration, and then mixed with human IgE (1 μg/mL). Then, incubation was performed at room temperature for 30 minutes to prepare samples. In addition, mast cells derived from and differentiated from mouse bone marrow, in which a human FcεRI gene had been introduced and the mouse FcεRI gene had been removed, were prepared. The prepared mast cells were washed with HBSS buffer, and then 5×10$^5$ cells were refloated into 60 μL of HBSS buffer.

Then, 20 μL of the sample thus prepared was added to the mast cells, and then incubated in a 5% $CO_2$ incubator at 37° C. for 30 minutes. Subsequently, after 20 μL of human anti-IgE antibody (BioLegend, Cat No. 325502, 0.5 μg/mL) was added, the resultant was incubated again in 5% $CO_2$ incubator at 37° C. for 30 minutes. Then, after centrifugation at 1,500 rpm at 4° C., 30 μL of the supernatant was separated. 30 μL of the separated supernatant and 30 μL of the substrate (4-nitrophenyl N-acetyl-β-glucosaminide, 5.84 mM) were mixed well, and then incubated in a 5% $CO_2$ incubator at 37° C. for 25 minutes. Then, 140 μL of 0.1 M sodium carbonate buffer (pH 10) was added to terminate the reaction. Thereafter, absorbance at 405 nm was measured to compare relative amounts of secreted β-hexosaminidase, and an inhibitory effect against mast cells was identified depending on each concentration of the sample. The results are shown in FIG. 8.

Figure 8:
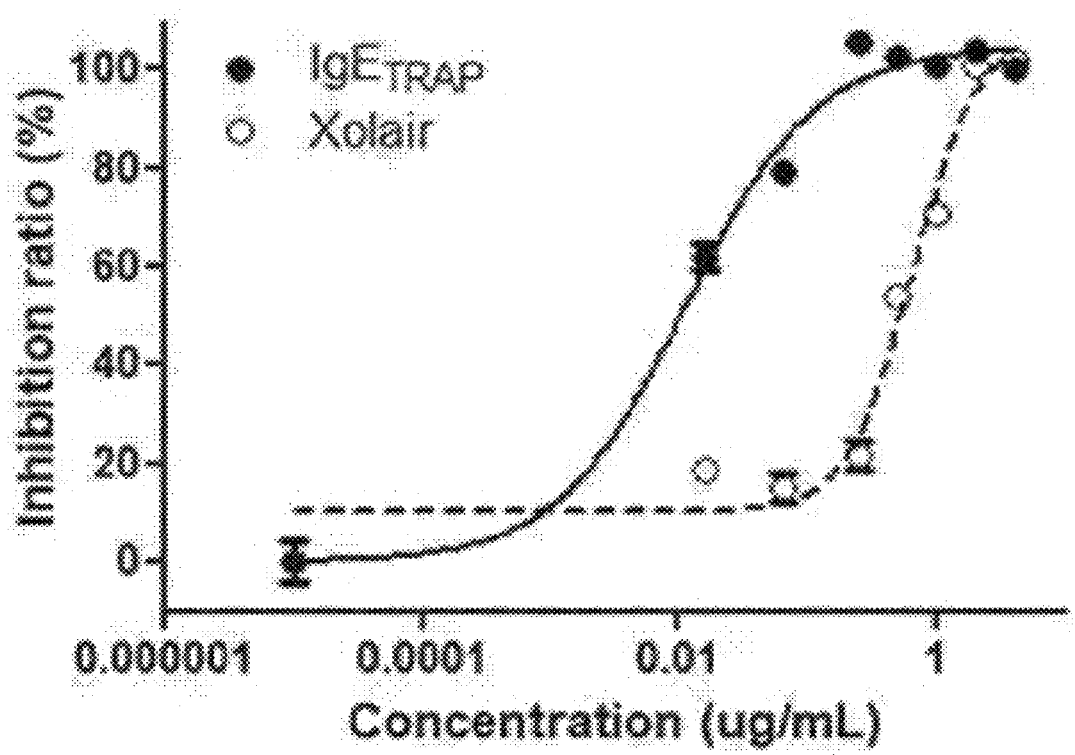
FIG. 8 is a view showing a comparison between inhibitory abilities, on activity of human FcεRI-expressing mouse-derived mast cells, of the polypeptide dimer ($IgE_{TRAP}$) according to an embodiment of the present invention and Xolair (omalizumab) depending on concentrations thereof.

As shown in FIG. 8, IC$_{50}$ of the polypeptide dimer was measured to be approximately 11.16 ng/mL, and IC$_{50}$ of Xolair was measured to be approximately 649.8 ng/mL. Therefore, it was identified that the polypeptide dimer has a 58-fold higher inhibitory ability on mast cell activity than Xolair.

Experimental Example 6. Confirmation of Activity of Polypeptide Dimer Through In Vivo Assay in Food Allergy Model 50 μg of ovalbumin (OVA) and 1 mg of alum were intraperitoneally administered to Balb/c mice (Orientbio Inc.) two times at a 14-day interval to induce sensitization. Thereafter, 50 mg of OVA was orally administered five times in total on days 28, 30, 32, 34, and 36, to induce food allergy in intestines.

After the OVA was orally administered two times, that is, on day 31, the mice were divided into three groups, each containing 7 mice. The three divided groups were as follows: Group 1 receiving the polypeptide dimer (FcεRIαECD-Fc2ST) at a high concentration (200 μg), Group 2 receiving the polypeptide dimer (FcεRIαECD-Fc2ST) at a low concentration (20 μg), and Group 3 receiving nothing.

While orally administering the OVA, it was observed whether diarrhea occurs due to food allergy induction. In addition, the mice were sacrificed on day 37, and the number of mast cells in the small intestine, the IgE concentration in blood, and the concentration of the mast cell degranulation enzyme (mast cell protease-1 (MCPT-1)) in blood were analyzed for the mice belonging to each group.

Figure 9:
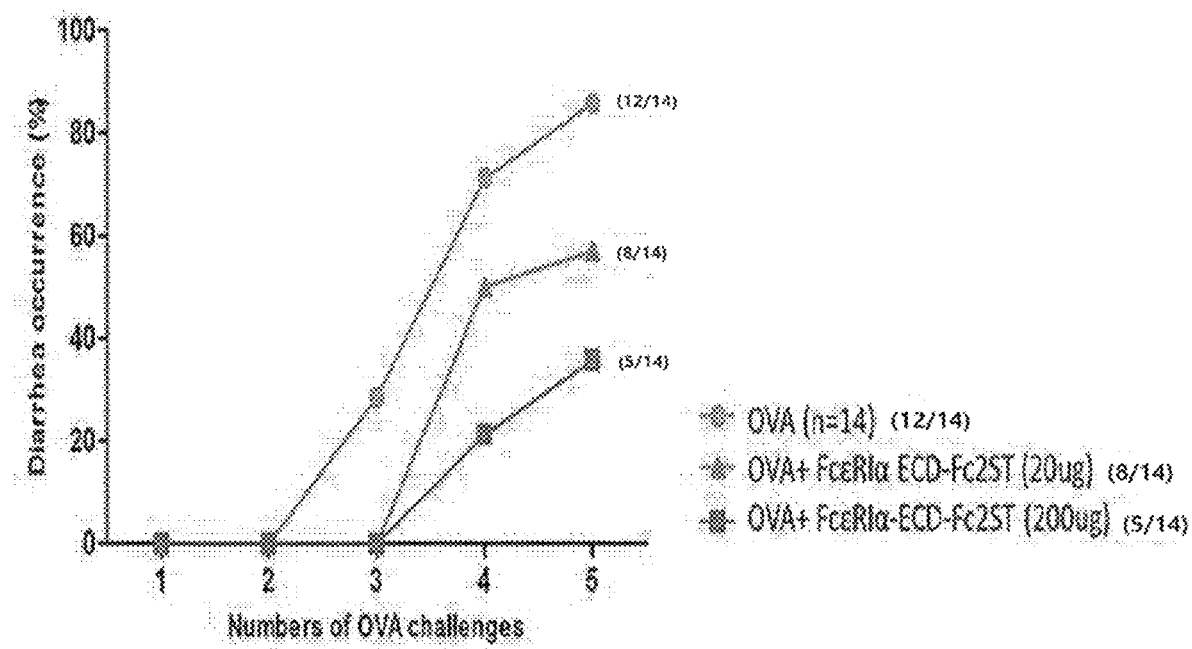
FIG. 9 is a view confirming the anti-allergic effect of a polypeptide dimer according to an embodiment of the present invention by measuring the frequency of diarrhea in a food allergy model.

As a result, as shown in FIG. 9, diarrhea occurred in mice of Group 3 after the second oral administration of OVA. On the other hand, diarrhea occurred in mice of Group 1 and Group 2 after the third oral administration of OVA. In particular, the frequency of diarrhea in mice of Group 1 was lower than that in mice of Group 2. Through this, it was confirmed that the effect against food allergy increased in proportion to the concentration of a polypeptide dimer.

Experimental Example 7. Analysis of Content of Sialic Acid of Polypeptide Dimer

Based on the aspects that the production rate of the polypeptide produced from the FcεRIαECD-Fc2+a2,6-ST cell line prepared in Example 1 above is the highest, and the anti-allergic effect of the polypeptide dimer (FcεRIαECD-Fc2ST) in Experimental Examples 4 to 6 is excellent, the sialic acid content of the polypeptide dimer was analyzed to investigate the anti-allergic efficacy of the polypeptide dimer depending on the sialic acid content.

Specifically, in order to measure the sialic acid content contained in the glycan structure of the polypeptide dimer (FcεRIαECD-Fc2ST) produced from the FcεRIαECD-Fc2+a2,6-ST cell line prepared in Example 1 above, sialic acid was first separated by treatment with sialidase, which is an enzyme associated with sialic acid catabolism. Thereafter, the separated sialic acid was isolated, detected and quantified using HPLC (waters, alliance e2659).

The polypeptide dimer was divided into three samples according to the pH gradient, and isolated and purified. Three samples were placed in an AmiconUltra 10K (Millipore, UFC501096) filter, and centrifuged for 10 minutes under a condition of 13,000 rpm, 4° C. temperature, and repeated 5 times, and the concentrate was exchanged with deionized water and concentrated. The concentration of the sample was set to 10 mg/mL or more when measured at a wavelength of 280 nm.

Thereafter, 0.5 mg of each sample was taken and placed in an EP tube, and 1 μL of sialidase (Roche, 10 269 611 001) and 40 μL of sodium phosphate buffer (pH 7.0) at a concentration of 10 mM were added, and then deionized water was added so that the final volume was 100 μL. 2 μL of each sample was taken to measure the concentration at a wavelength of 280 nm, and the confirmed concentration value was used as the final analysis concentration.

The sample was reacted for 18 hours in a 37° C. incubator, and then placed in an AmiconUltra 10K filter, and centrifuged for 15 minutes under a condition of 13,000 rpm, 4° C., and the filtrate passing through a filter was used for analysis. HPLC analysis conditions are shown in Table 4 below.

TABLE 4

| | |
|---|---|
| Analysis Column | RHM-monosaccharide H+ (8%) 300 × 7.8 mm (Rezex); analysis column |
| | RHM-monosaccharide H+ (8%) 50 × 7.8 mm (Rezex); guard column |
| Standard Substance | NGNA: 2~40 μM NANA: 100~2000 μM |
| Flux | 0.55 ml/min |

TABLE 4-continued

| | |
|---|---|
| Column Temperature | 50° C. |
| Detection | 206 nm |
| Injection Volume | 5 μL |
| Mobile Phase | 5 mN sulfuric acid in water |
| Gradient/Time | Isocratic Elution/45 minutes |

The standard substance for calculating the content of sialic acid is a mixture of N-acetylneuraminic acid (hereinafter referred to as NANA) and N-glycolylneuraminic acid (hereinafter referred to as NGNA). The linear regression equation for the standard curve was obtained to calculate the molar concentrations of NGNA and NANA in the analyte. The mixtures used are shown in Table 5 below.

TABLE 5

| Mixture | 1 | 2 | 3 | 4 | 5 |
|---|---|---|---|---|---|
| NANA (μM) | 2,000 | 1,000 | 500 | 300 | 200 |
| NGNA (μM) | 40 | 20 | 10 | 6 | 4 |

The NANA sialic acid content in the sample was calculated using the NANA content. The sialic acid content in the sample was expressed as a molar ratio of sialic acid/sample (mol/mol).

Sialic acid content of Sample = [Equation 1]

(molar concentration of $NANA$ in sample)/

(Molar concentration of sample)

In addition, the content of NGNA in the sample was calculated using the NGNA content. The content of NGNA in the sample was expressed as a molar ratio of NGNA/analyte (mol/mol).

$NGNA$ Content of sample = [Equation 2]

($NGNA$ molar concentration in analyte)/

(Molar concentration of analyte)

The results are shown in Table 6 below.

TABLE 6

| Sample | | NGNA/Protein (mol/mol) | NANA/Protein (mol/mol) |
|---|---|---|---|
| FcεRIαECD-Fc2ST | Sample 1 ($SA^{low}$) | 0.13 | 7.7 |
| | Sample 2 ($SA^{medi}$) | 0.17 | 12.0 |
| | Sample 3 ($SA^{high}$) | 0.27 | 19.1 |

As shown in Table 6, it was divided into three samples according to the pH gradient, and separated and purified, and the sialic acid content in the samples was measured differently. In order to compare the anti-allergic efficacy according to the sialic acid content, a polypeptide dimer is referred to as "$SA^{low}$", "$SA^{medi}$" and "$SA^{high}$" in order of the sialic acid content.

Experimental Example 8. Confirmation of Change in Dimer Formation of Polypeptide According to Sialic Acid Content In order to confirm whether there was a change in dimer formation of the polypeptide according to the sialic acid content, $SA^{low}$, $SA^{medi}$ and $SA^{high}$ separated in Example 9 were subjected to SDS-PAGE analysis under a non-reducing condition and a reducing condition in the same manner as in Experimental Example 1.

Figure 10:
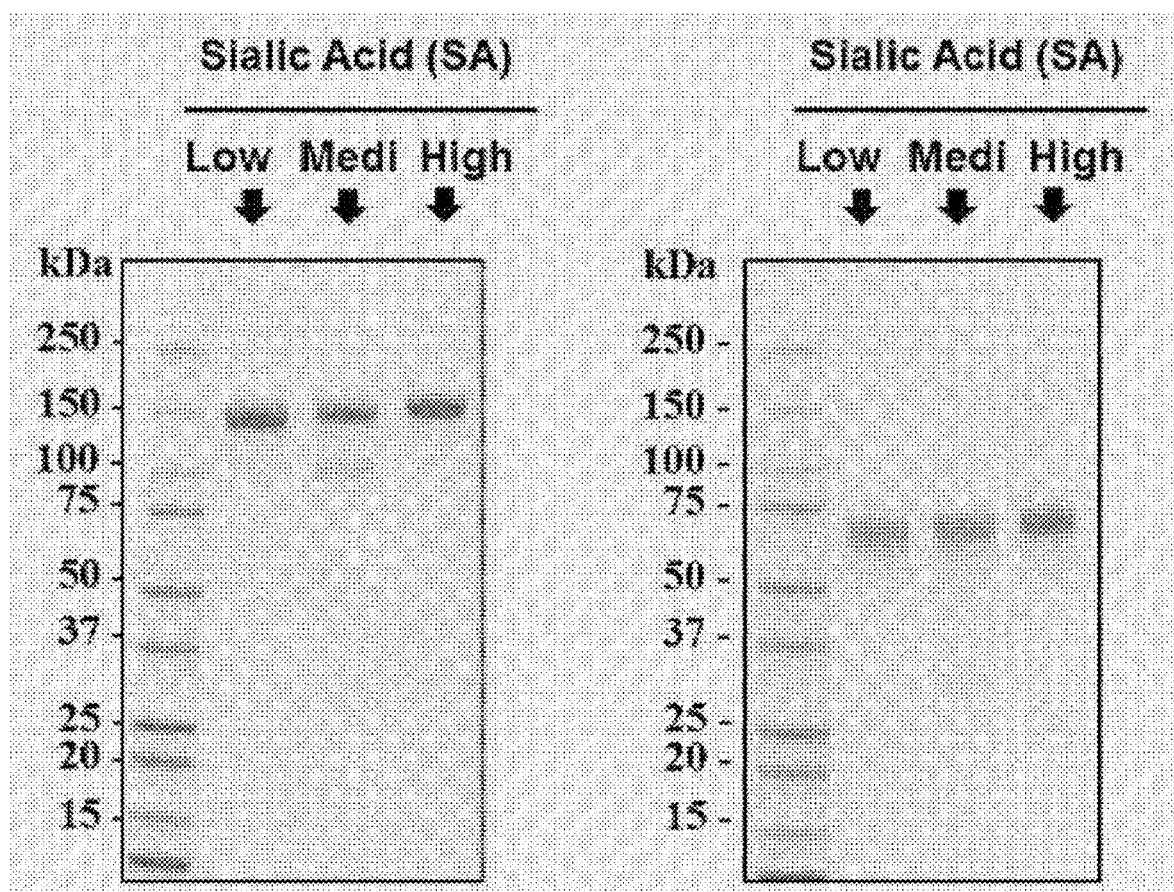
FIG. 10 is a view showing SDS-PAGE results for a non-reduced form and a reduced form of a polypeptide dimer according to an embodiment of the present invention ($SA^{low}$, $SA^{medi}$ and $SA^{high}$).

As a result, in all $SA^{low}$O, $SA^{medi}$ and $SA^{high}$, a polypeptide having a size of about 150 kDa was detected under a non-reducing condition, and a polypeptide having a size of about 75 kDa was detected under a reducing condition. Through this, it was confirmed that the polypeptide forms a dimer (FIG. 10).

Experimental Example 9. Confirmation of Isoelectric Point of Polypeptide Dimer According to Sialic Acid Content In order to confirm whether the isoelectric point of the polypeptide dimer changes according to the sialic acid content, $SA^{low}$, $SA^{medi}$ and $SA^{high}$ Separated in Experimental Example 7 were mixed with the IEF sample solution, and then loaded into a pH 3-7 IEF gel (Invitrogen), and electrophoresis was sequentially performed for 1 hour under a 100V condition, for 1 hour under a 200V condition, and for 30 minutes under a 500V condition. After the electrophoresis was completed, the gel was reacted in a fixing solution comprising 12% trichloroacetic acid and 3.5% sulfosalicylic acid for 30 minutes, and then washed with distilled water. A protein was stained with a Coomassie Brilliant Blue solution.

Figure 11:
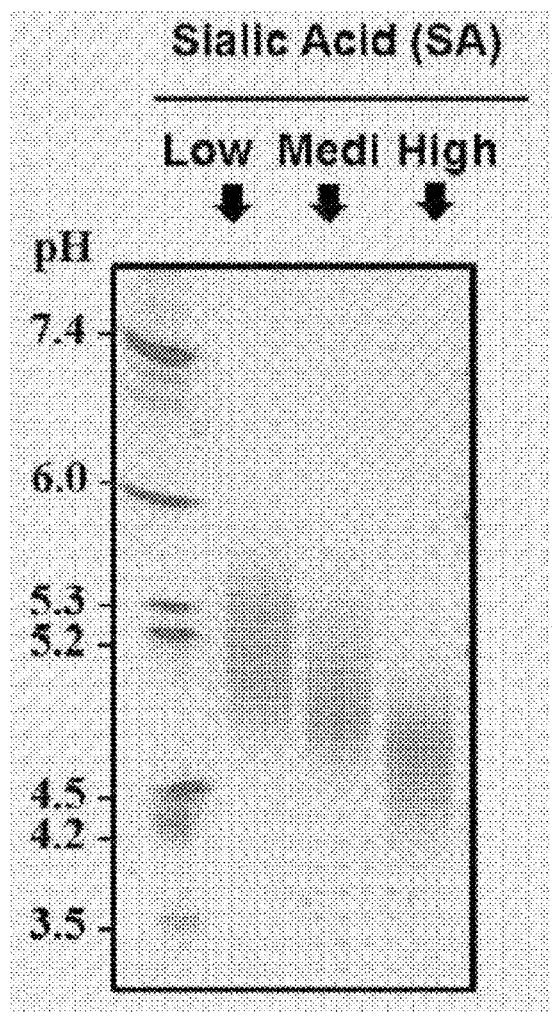
FIG. 11 is a view confirming the isoelectric point of a polypeptide dimer according to an embodiment of the present invention ($SA^{low}$, $SA^{medi}$ and $SA^{high}$).

As a result, the isoelectric points of $SA^{low}$, $SA^{medi}$ and $SA^{high}$ were slightly different according to the sialic acid content, and were found to be about 5.3, 4.9 and 4.7, respectively (FIG. 11).

Experimental Example 10. Confirmation of Anti-Allergic Activity of Polypeptide Dimer According to Sialic Acid Content in Food Allergy Animal Model: Measurement of Frequency of Diarrhea In order to confirm whether the activity of the polypeptide dimer changes according to the sialic acid content, sensitization was induced by intraperitoneal administration of 50 μg of OVA and 1 mg of alum twice at an interval of 14 days for Balb/c mice (Orient Bio). Thereafter, at Day 28, 30, 32, 34, 36, 38, 40 over a total of 7 times, food allergy was induced by oral administration of 50 mg of OVA. In this case, the oral administration of OVA was performed after fasting for 4 hours.

The OVA was administered orally twice, and then at Day 40, the mice were divided into 3 groups of 7 mice. The mice were divided into Group 1, a group in which a polypeptide dimer having a high content of sialic acid ($SA^{high}$) is subcutaneously administered at a high concentration (200

μg), Group 2, a group in which a polypeptide dimer having a low content of sialic acid ($SA^{low}$) is subcutaneously administered at a high concentration (200 μg), and Group 3, a group in which PBS is subcutaneously administered. It was confirmed whether diarrhea occurred according to the induction of food allergy when the OVA was administered orally.

Figure 12:
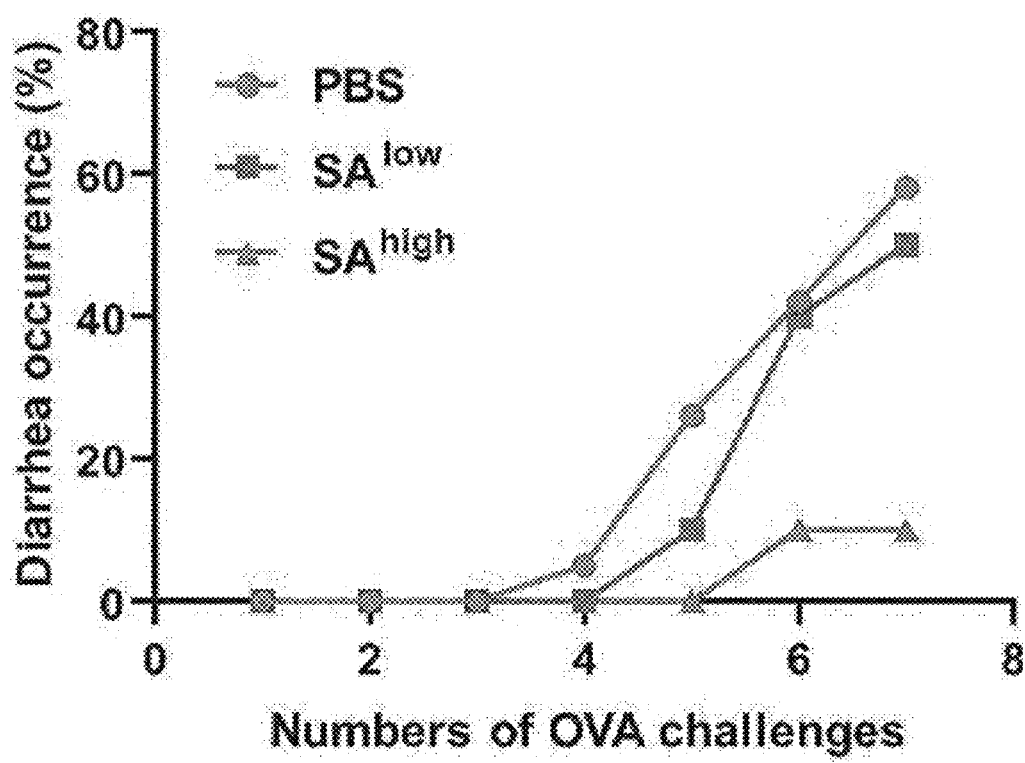
FIG. 12 is a view confirming the anti-allergic effect of subcutaneous injection of a polypeptide dimer according to an embodiment of the present invention ($SA^{low}$ and $SA^{high}$) by measuring the frequency of diarrhea in a food allergy model.

As a result, diarrhea occurred in mice of Group 3 after the fourth oral administration of OVA. Diarrhea occurred in mice of Group 2 after the fifth oral administration of OVA. In particular, the frequency of diarrhea increased rapidly in mice of Group 2 after the sixth oral administration of OVA. On the other hand, diarrhea occurred in mice of Group 1 after the sixth oral administration of OVA, but the frequency of diarrhea was maintained but did not increase in mice of Group 1 even after the seventh oral administration of OVA (FIG. 12). Through this, it was confirmed that the polypeptide dimer having a high content of sialic acid ($SA^{high}$) had an excellent anti-allergic effect compared to the polypeptide dimer having a low content of sialic acid ($SA^{low}$).

Experimental Example 11. Confirmation of Anti-Allergic Activity of Polypeptide Dimer According to Sialic Acid Content in Food Allergy Animal Model: Measurement of IgE Concentration in Blood The blood was collected by orbital sampling method from mice of each group in which the seventh oral administration of OVA of Experimental Example 10 was performed. After reacting for 30 minutes at ambient temperature, serum was separated by centrifugation for 15 minutes under a condition of 13,000 rpm at a temperature of 4° C. In order to measure free IgE concentration in the blood, mouse total IgE ELISA kit (BioLegend) was used, and in this case, ELISA was performed according to the manufacturer's protocol except that a polypeptide dimer ($SA^{low}$ and $SA^{high}$) according to an embodiment of the present invention was used as a substance coated on a 96-well-plate instead of an anti-IgE antibody.

Specifically, a 96-well-plate was coated with a polypeptide dimer ($SA^{low}$ and $SA^{high}$) diluted with PBS, and reacted overnight at a temperature of 4° C. The next day, after washing with PBS containing 0.05% tween 20 (hereinafter, washing buffer), a blocking buffer (assay diluent) was added and reacted for 1 hour. Thereafter, it was washed with a washing buffer, and then the mouse IgE to be used as a standard solution and the serum samples of mice were diluted in a 1× assay diluent, and placed in a plate and reacted for 2 hours.

After washing again with a washing buffer, biotin-labeled mouse anti-IgE antibody was added and reacted for 1 hour. After washing with a washing buffer, HRP (horse radish peroxidase)-labeled avidin (Avidin-HRP) was added and reacted for 30 minutes. After washing with a washing buffer, a substrate solution was added and reacted for 20 minutes while blocking light, and then a stop solution (1 M $H_2SO_4$) was added to stop the reaction. Thereafter, the absorbance value was measured at a wavelength of 450 nm with a microplate reader (Epoch Microplate Spectrophotometer), and the concentration was calculated.

As a result, for the mice of Group 3 in which PBS was subcutaneously administered, the IgE concentration in the blood was calculated to be about 8,000 ng/mL. In addition, for the mice of Group 2 in which a polypeptide dimer having a low content of sialic acid ($SA^{low}$) was subcutaneously administered, the IgE concentration in the blood was calculated to be about 7,000 ng/mL. On the other hand, for the mice of Group 1 in which a polypeptide dimer having a high content of sialic acid ($SA^{high}$) was subcutaneously administered, the IgE concentration in the blood was calculated to be about 4,900 ng/mL, and there was a significant difference from the IgE concentration values in the blood between mice of Group 2 and Group 3 (FIG. 13).

From these results, it was found that when the polypeptide dimer having a high content of sialic acid was administered subcutaneously, the IgE content in the blood was reduced. In addition, based on such reduction of IgE in the blood, it was predicted that the polypeptide dimer having a high content of sialic acid is effective in treating allergy.

Experimental Example 12. Confirmation of Anti-Allergic Activity of Polypeptide Dimer According to Sialic Acid Content in Food Allergy Animal Model: Measurement of MCPT-1 Concentration in Blood Serum was prepared by taking blood from mice of each group 2 days after the food allergy experiment was completed. In order to measure the MCPT-1 (Mast Cell Protease-1) concentration in the blood, an MCPT-1 ELISA kit (Invitrogen) was used to perform the procedure according to the manufacturer's protocol.

Specifically, a 96-well-immunized plate was coated with a mouse anti-MCPT-1 antibody and reacted overnight at a temperature of 4° C. The next day, after washing with PBS containing 0.05% tween 20 (hereinafter, washing buffer), PBS containing 1% BSA (bovine serum albumin) (hereinafter, blocking buffer, assay diluent) was added and reacted for 1 hour. Thereafter, it was washed with a washing buffer, and then the MCPT-1 to be used as a standard solution and the serum samples of mice were diluted in a 1× assay diluent, and placed in a plate and reacted for 2 hours.

After 2 hours, a biotin-labeled mouse anti-MCPT-1 antibody was added and reacted for 1 hour. After washing with a washing buffer, HRP (horse radish peroxidase)-labeled avidin (Avidin-HRP) was added and reacted for 30 minutes. After washing with a washing buffer, a substrate solution was added and reacted for 20 minutes while blocking light, and then a stop solution (1 M $H_2SO_4$) was added to stop the reaction. Thereafter, the absorbance value excluding that measured at a wavelength of 570 nm wavelength from that measured at a wavelength of 450 nm was determined with a microplate reader (Epoch Microplate Spectrophotometer) and the concentration was calculated.

As a result, for the mice of Group 3 in which PBS was subcutaneously administered, the MCPT-1 concentration in the blood was calculated to be about 4,000 ng/mL. In addition, for the mice of Group 2 in which a polypeptide dimer having a low content of sialic acid ($SA^{low}$) was subcutaneously administered, the MCPT-1 concentration in the blood was calculated to be about 4,200 ng/mL. On the other hand, for the mice of Group 1 in which a polypeptide dimer having a high content of sialic acid ($SA^{high}$) was subcutaneously administered, the MCPT-1 concentration in the blood was calculated to be about 2,800 ng/mL, and there was a significant difference from the MCPT-1 concentration values in the blood between mice of Group 2 and Group 3 (FIG. 14).

Example 3. Preparation of Polypeptide Dimer Having High Content of Sialic Acid Through Purification In order to confirm the physical properties of a polypeptide dimer according to the sialic acid content, a polypeptide dimer containing a wide range of sialic acid was obtained. Specifically, a polypeptide dimer obtained from the FcεRIαECD-Fc2+a2,6-ST cell line was purified using affinity chromatography and anion exchange chromatography.

First, the cell culture solution was subjected to affinity chromatography to remove the primary impurities from the culture solution. The affinity chromatography was performed using Amsphere™ A3 pre-packing column (bed height 5 cm, volume 5 mL) packed with Amsphere™ A3 resin and AKTA Avant 25 equipment, a liquid chromatography system. Here, it was performed using 100 mM Glycine, pH 3.3 as an eluted buffer.

Thereafter, the anion exchange chromatography was performed using Hiscreen QFF (bed height 10 cm, volume 5 mL) packed with Q Sepharose Fast Flow resin and AKTA Avant 25 equipment, a liquid chromatography system. 20 mM phospho-citrate, pH 3.5 was used as an eluted buffer. In this case, the concentration of 20 mM phospho-citrate, pH 4.0, as a washing buffer, was adjusted to obtain dimers having various sialic acid contents. Analysis of the sialic acid content was performed by the analysis method used in Experimental Example 7. Through this, polypeptide dimers having a sialic acid content of 7.0 mol/mol, 10.3 mol/mol, 12.9 mol/mol, 14.9 mol/mol and 21.4 mol/mol were obtained.

Experimental Example 13. Pharmacokinetics Analysis of Polypeptide Dimer According to Sialic Acid Content in Mouse Model In order to perform pharmacokinetics analysis according to the sialic acid content of the polypeptide dimer, the polypeptide dimers having a sialic acid content of 7.0 mol/mol, 10.3 mol/mol, 12.9 mol/mol, 14.9 mol/mol and 21.4 mol/mol prepared in Example 3 was subcutaneously injected into mice at a concentration of 10 mg/kg, respectively. In order to analyze the pharmacokinetics of the polypeptide dimer, the blood was collected at Hour 0, Hour 3, Hour 10, Hour 24, Hour 72, Hour 168, and Hour 240 after administration of the substance and analyzed in the following manner.

The anti-FcεRI antibody (Invitrogen) was diluted in 1×PBS (Welgene) at a concentration of 0.5 μg/mL, and added to an immunoplate (Thermo), and reacted overnight under a condition of 4° C. After the reaction was completed, the immunoplate was washed with 1×PBST, and I-Block solution (Invitrogen), a blocking solution, was added per well and reacted at ambient temperature for 1 hour. During blocking, standard and analytical samples were prepared. The polypeptide dimer was diluted in 1% BSA/PBS containing mouse blank serum at a concentration of 0.19 ng/mL to 200 ng/mL to prepare a standard substance, and the dilution with 1/20-1/300 using 1% BSA/PBS containing the blank serum was also performed to prepare an analytical sample.

Figure 15:
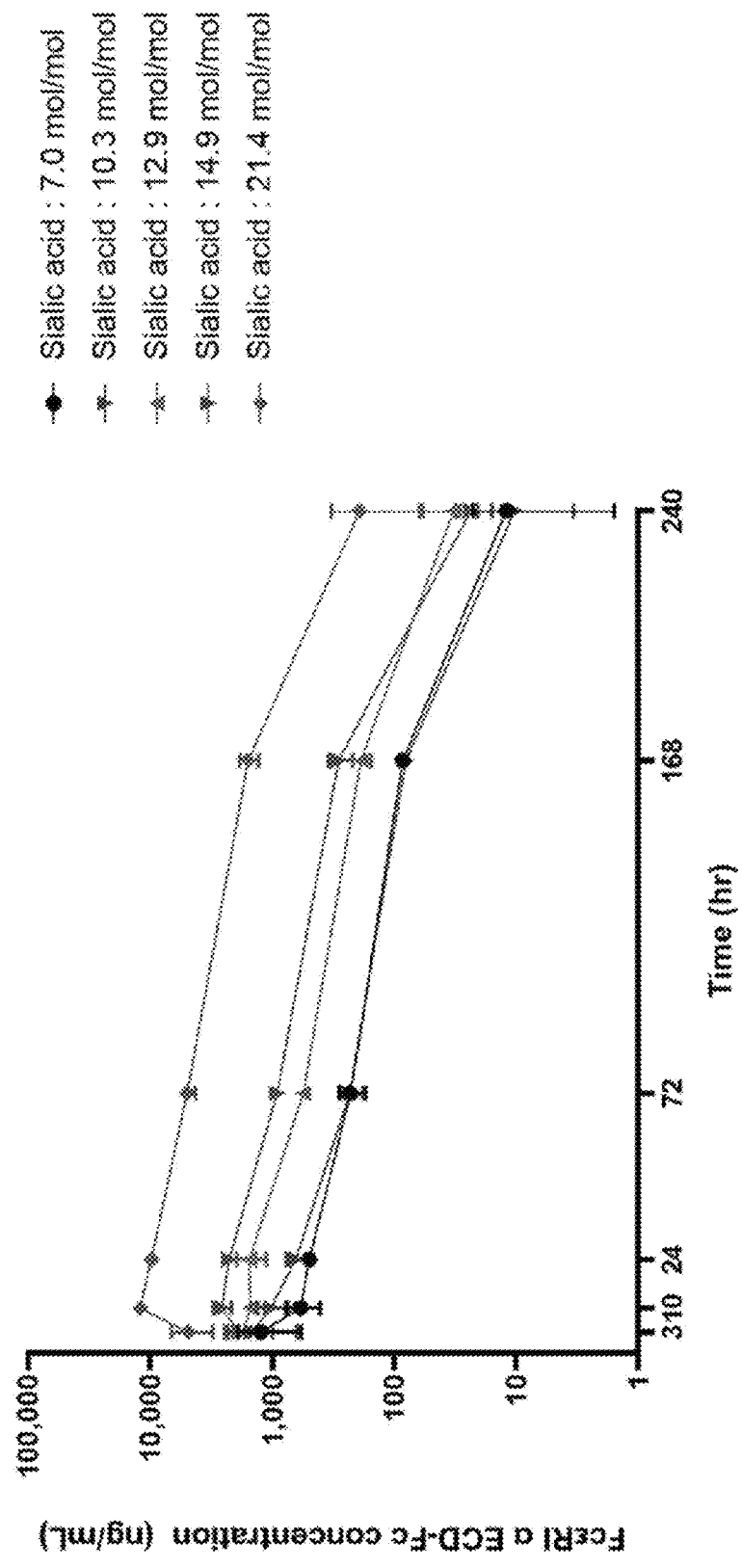
FIG. 15 is a view showing the results of analysis of a pharmacokinetic profile of a polypeptide dimer according to one embodiment depending on sialic acid content in a mouse model.

After the blocking was completed, the plate was washed with 1×PBST, and the prepared standard and analytical samples were added per well, and then reacted at ambient temperature for 1 hour. Thereafter, it was washed with 1×PBST, and an anti-human IgG4-HRP (Southern biotech) diluted to 1:10,000 was added, and then reacted at ambient temperature for 1 hour. After the reaction was completed, the plate was washed with 1×PBST, and TMB solution (Thermo) was added to the well and reacted. When the absorbance value was measured in the range of 0.8-1.0 at a wavelength of 650 nm using a microplate reader (Molecular devices), a stop solution (Sigma) was added per well to stop the reaction. After the reaction was terminated, the absorbance was measured in the plate at a wavelength of 450 nm within 5 minutes and the numerical values were analyzed. The resulting pharmacokinetic graph and pharmacokinetic parameters of the polypeptide dimer according to the sialic acid contents are shown in FIG. 15 and Table 7.

As a result, as shown in Table 7, it was confirmed that the higher the sialic acid content of the polypeptide dimer administered to the mouse, the higher the concentration in the blood.

TABLE 7

| sialic acid content (mol/mol) | $T_{1/2}$ (hr) | $T_{max}$ (hr) | $C_{max}$ (μg/ml) | $AUC_{last}$ (hr*μg/ml) |
|---|---|---|---|---|
| 7.0 | 51.3 ± 5.9 | 5.3 ± 3.3 | 1.3 ± 0.5 | 47.8 ± 3.2 |
| 10.3 | 44.5 ± 6.7 | 5.3 ± 3.3 | 1.6 ± 0.6 | 57.1 ± 9.6 |
| 12.9 | 40.0 ± 9.5 | 17 ± 9.9 | 2.0 ± 0.4 | 119.7 ± 5.2 |
| 14.9 | 35.4 ± 3.5 | 7.7 ± 3.3 | 2.6 ± 0.3 | 182.7 ± 7.0 |
| 21.4 | 38.5 ± 5.0 | 10.0 ± 0.0 | 12.1 ± 0.9 | 890.0 ± 64.4 |

Experimental Example 14. Confirmation of Efficacy According to Sialic Acid Content of Polypeptide Dimer in Passive Systemic Anaphylaxis Mouse Model In order to confirm the difference in an anti-allergic effect in vivo according to the sialic acid content of the polypeptide dimer, the method disclosed in the literature was applied to induce the passive systemic anaphylaxis (PSA) in mice in the manner as follows (Methods and Protocols, Methods in Molecular Biology, vol. 1032, DOI 10.1007/978-1-62703-496-8_10). It is known that mast cells are activated by induction of anaphylaxis and body temperature is reduced by increasing mast cells. While inducing PSA in mice using this, the polypeptide dimer having the respective sialic acid content was administered, and then the body temperature was measured to compare the anti-allergic effect.

Figure 16:
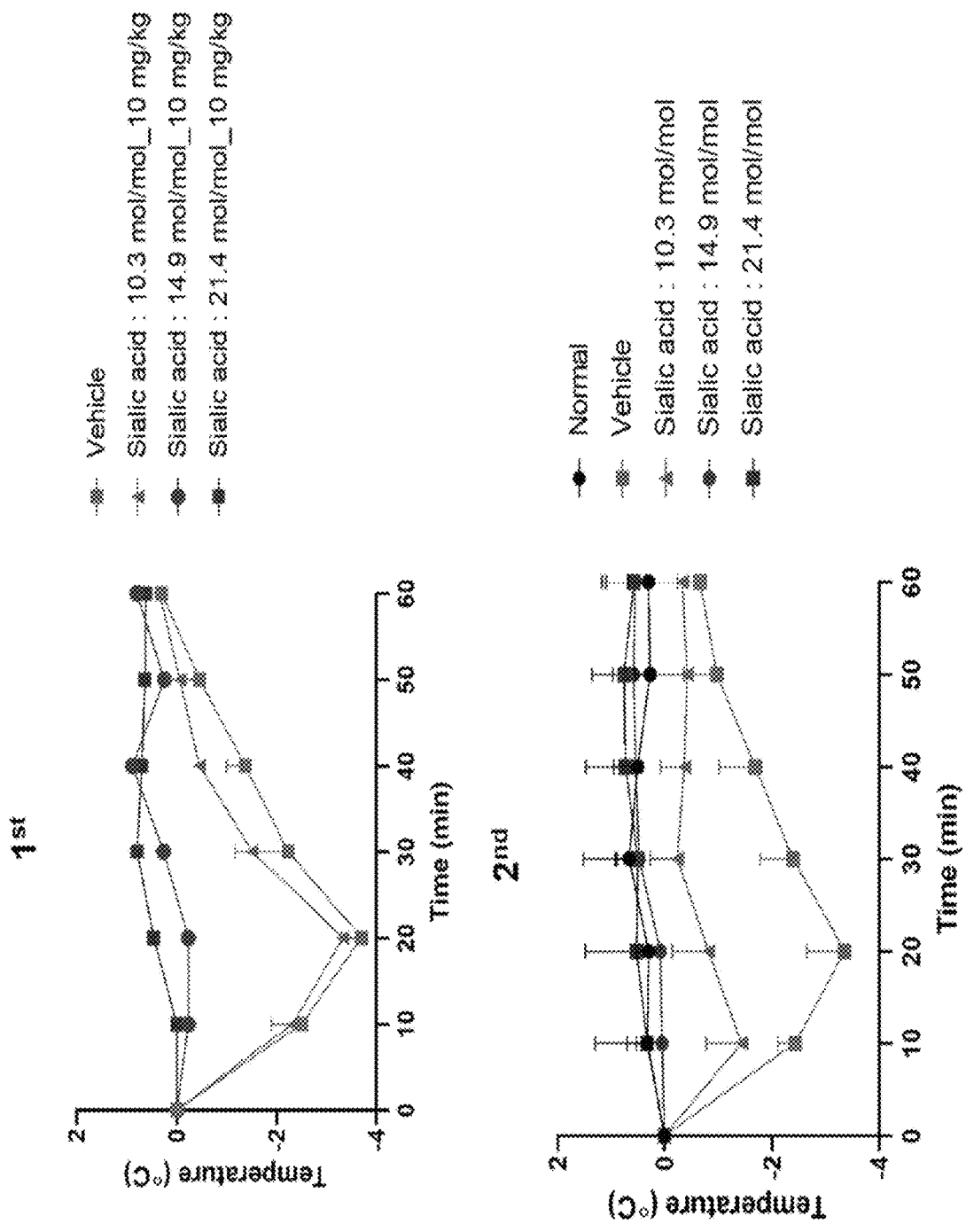
FIG. 16 is a view confirming the anti-allergic effect of a polypeptide dimer according to one embodiment depending on sialic acid content by measuring the body temperature in a passive systemic anaphylaxis mouse model.

The body temperature was measured in transponder-inserted Balb/c mice (Orient Bio), and then 20 μg of anti-DNP IgE (Sigma) containing 0.9% NaCl was intraperitoneally administered, and then the polypeptide dimers having different sialic acid contents, respectively, were subcutaneously administered at 10 mg/kg. After 24 hours, the body temperature of the mice was measured before DNP-HAS (Sigma) containing 0.9% NaCl, a foreign antigen, was administered. Thereafter, 1 mg of the antigen was administered intravenously. After administration, the body temperature of the mice was measured at an interval of 10 minutes for 1 hour using a remote body temperature meter (Bio medic data systems). The experimental results are shown in FIG. 16.

As a result, it was confirmed that the body temperature of the mice was reduced in groups in which a vehicle and a polypeptide dimer having a sialic acid content of 10.3 mol/mol were administered, and the body temperature of the mice was not reduced in groups in which the polypeptide dimer having a sialic acid content of 14.9 mol/mol or more was administered. Through this, it was confirmed that a polypeptide dimer having a high content of sialic acid has an excellent effect of reducing the induction of passive systemic anaphylaxis compared to a polypeptide dimer having a low content of sialic acid.

The invention claimed is:

1. A polypeptide dimer comprising:
a first monomer comprising an extracellular domain of an alpha subunit of an IgE Fc receptor (FcεRIα-ECD),
a second monomer comprising an extracellular domain of an alpha subunit of an IgE Fc receptor (FcεRIα-ECD),
wherein the FcεRIα-ECD of the first and second monomers comprises the amino acid sequence of SEQ ID NO: 1,
wherein the first monomer and the second monomer each contain an Fc region, and
wherein the Fc region and the FcεRIα-ECD, in the first and second monomers, are linked via a hinge, and
wherein the polypeptide dimer comprises sialic acid and, a molar ratio of the sialic acid to the polypeptide dimer is 12 to 25.

2. The polypeptide dimer according to claim 1,
wherein the Fc region of the first and second monomers comprises the amino acid sequence of SEQ ID NO: 2.

3. The polypeptide dimer according to claim 1,
wherein the hinge of the first and second monomers is a hinge region derived from immunoglobulin IgD or a variant thereof.

4. The polypeptide dimer according to claim 3,
wherein the hinge region derived from immunoglobulin IgD or a variant thereof contains at least one cysteine.

5. The polypeptide dimer according to claim 3,
wherein the hinge region derived from immunoglobulin IgD or a variant thereof comprises the sequence of

```
                                            (SEQ ID NO: 17)
Arg Asn Thr Gly Arg Gly Gly Glu Glu Lys Lys Xaa1

Xaa2 Lys Glu Lys Glu Glu Gln Glu Glu Arg Glu Thr

Lys Thr Pro Glu Cys Pro,
``` wherein Xaa1 is Lys or Gly, and
Xaa2 is Glu, Gly, or Ser; or

```
                                            (SEQ ID NO: 18)
Ala Gln Pro Gln Ala Glu Gly Ser Leu Ala Lys Ala Thr

Thr Ala Pro Ala Thr Thr Arg Asn Thr Gly Arg Gly Gly

Glu Glu Lys Lys Xaa3 Xaa4 Lys Glu Lys Glu Glu Gln

Glu Glu Arg Glu Thr Lys Thr Pro Glu Cys Pro,
``` wherein Xaa3 is Lys or Gly, and
Xaa4 is Glu, Gly, or Ser.

6. The polypeptide dimer according to claim 3,
wherein the hinge region derived from immunoglobulin IgD or a variant thereof comprises any one amino acid sequence selected from the group consisting of SEQ ID NO: 3, SEQ ID NO: 4, and SEQ ID NO: 19.

7. The polypeptide dimer according to claim 1,
wherein the sialic acid is N-acetylneuraminic acid.

8. A composition comprising a polypeptide dimer according to claim 1.

9. The composition according to claim 8, wherein the composition is for subcutaneous injection.

10. The composition according to claim 8, which is a pharmaceutical composition or a food composition.

11. The composition according to claim 8, wherein the composition is a pharmaceutical composition in a form of a transdermal patch or topical patch.

12. The composition according to claim 8,
wherein the Fc region of the first and second monomers comprises the amino acid sequence of SEQ ID NO: 2; and
wherein the hinge is a hinge region derived from immunoglobulin IgD or a variant thereof, and
wherein the sialic acid is N-acetylneuraminic acid.

13. The composition according to claim 8,
wherein the hinge region derived from immunoglobulin IgD or a variant thereof comprises the sequence of

```
                             (SEQ ID NO: 17)
Arg Asn Thr Gly Arg Gly Gly Glu Glu Lys Lys Xaa1

Xaa2 Lys Glu Lys Glu Glu Gln Glu Glu Arg Glu Thr

Lys Thr Pro Glu Cys Pro,
``` wherein Xaa1 is Lys or Gly, and
Xaa2 is Glu, Gly, or Ser; or

```
                             (SEQ ID NO: 18)
Ala Gln Pro Gln Ala Glu Gly Ser Leu Ala Lys Ala Thr

Thr Ala Pro Ala Thr Thr Arg Asn Thr Gly Arg Gly Gly

Glu Glu Lys Lys Xaa3 Xaa4 Lys Glu Lys Glu Glu Gln

Glu Glu Arg Glu Thr Lys Thr Pro Glu Cys Pro,
``` wherein Xaa3 is Lys or Gly, and
Xaa4 is Glu, Gly, or Ser.

\* \* \* \* \*